(12) United States Patent
de O Martins Ikari et al.

(10) Patent No.: US 10,988,428 B2
(45) Date of Patent: *Apr. 27, 2021

(54) PROCESS FOR THE RECOVERY OF KETONES AND GLYCOLS FROM FERMENTATION

(71) Applicant: Braskem S.A., Camaçari (BR)

(72) Inventors: Liliana Zanelli de O Martins Ikari, Campinas (BR); Fernanda Munhoz Anderle, Campinas (BR); Melina Gesteira Souza, Campinas (BR); Lucas Gualberto Santos Costa, Campinas (BR)

(73) Assignee: Braskem S.A., Camaçari (BR)

( * ) Notice: Subject to any disclaimer, the term of this patent is extended or adjusted under 35 U.S.C. 154(b) by 0 days.

This patent is subject to a terminal disclaimer.

(21) Appl. No.: 16/893,218

(22) Filed: Jun. 4, 2020

(65) Prior Publication Data

US 2020/0299218 A1 Sep. 24, 2020

Related U.S. Application Data

(63) Continuation of application No. 16/185,432, filed on Nov. 9, 2018, now Pat. No. 10,710,950.

(60) Provisional application No. 62/583,862, filed on Nov. 9, 2017.

(51) Int. Cl.

| | |
|---|---|
| *C07C 45/83* | (2006.01) |
| *C07C 29/76* | (2006.01) |
| *C07C 29/84* | (2006.01) |
| *B01D 1/00* | (2006.01) |
| *B01D 1/06* | (2006.01) |
| *B01D 3/00* | (2006.01) |
| *C07C 45/78* | (2006.01) |
| *C07C 45/82* | (2006.01) |
| *C07C 45/80* | (2006.01) |
| *C07C 45/81* | (2006.01) |
| *C07C 29/86* | (2006.01) |
| *C07C 29/92* | (2006.01) |
| *C12P 7/26* | (2006.01) |
| *C07C 29/80* | (2006.01) |
| *C07C 45/85* | (2006.01) |
| *C12P 7/18* | (2006.01) |

(52) U.S. Cl.
CPC .............. *C07C 45/83* (2013.01); *B01D 1/065* (2013.01); *B01D 3/002* (2013.01); *B01D 3/009* (2013.01); *C07C 29/76* (2013.01); *C07C 29/80* (2013.01); *C07C 29/84* (2013.01); *C07C 29/86* (2013.01); *C07C 29/92* (2013.01); *C07C 45/786* (2013.01); *C07C 45/80* (2013.01); *C07C 45/81* (2013.01); *C07C 45/82* (2013.01); *C07C 45/85* (2013.01); *C12P 7/18* (2013.01); *C12P 7/26* (2013.01)

(58) Field of Classification Search
CPC ......... C07C 45/50; C07C 45/83; C07C 29/76; C07C 29/84; B01D 1/065
See application file for complete search history.

(56) References Cited

U.S. PATENT DOCUMENTS

| | | | |
|---|---|---|---|
| 2,406,713 A * | 8/1946 | Senkus | 568/846 |
| 3,412,160 A * | 11/1968 | Schierholt | C07C 29/92 |
| | | | 568/868 |
| 2012/0322117 A1* | 12/2012 | Anton | C12P 7/18 |
| | | | 435/157 |

FOREIGN PATENT DOCUMENTS

| | | | | |
|---|---|---|---|---|
| DE | 933714 | * | 8/1963 | ............. C07C 29/00 |
| WO | WO-2012130316 A1 | * | 10/2012 | ............. C07C 29/80 |

* cited by examiner

*Primary Examiner* — Sikarl A Witherspoon
(74) *Attorney, Agent, or Firm* — Osha Bergman Watanabe & Burton LLP

(57) ABSTRACT

A method of obtaining ketones from a fermentation process may include collecting an off-gas and a fermented broth from a fermenter, transferring the off-gas from the fermenter to a ketone recuperation module and the fermented broth to a fluid separating module, and isolating the ketones from both the off-gas and the fermented broth. The off-gas and the fermented broth may both comprise a ketone.

36 Claims, 17 Drawing Sheets

PROCESS FOR THE RECOVERY OF KETONES AND GLYCOLS FROM FERMENTATION

BACKGROUND

Microbial fermentation produces a number of industrially-relevant compounds that may be used as feedstock for a diverse range of applications for polymer manufacture. Compounds of interest are generated as components of broth and off-gas exiting a fermentation vessel as product streams. Fermentation broth and off-gas are complex mixtures containing a wide range of components with very different characteristics, such as cellular biomass, insoluble solids, water, organic matter, inorganic and organic ions, and incondensable gases. The challenge lies in isolating product compounds from the various impurities, while minimizing time and energy costs associated with processing.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

In one aspect, embodiments disclosed herein relate to methods of obtaining ketones and glycols from a fermentation process, the method including: collecting an off-gas and/or a fermented broth from the fermenter, wherein the off-gas comprises a ketone, and wherein the fermented broth comprises one or more of glycol or ketone; and performing at least one of: transferring the off-gas from the fermenter to a ketone recuperation module; or transferring the fermented broth to a fluid separating module; and isolating one or more of: the ketone from the off-gas; and the glycol from the fermented broth.

Other aspects and advantages of the claimed subject matter will be apparent from the following description and the appended claims.

DETAILED DESCRIPTION

In one aspect, embodiments disclosed herein relate to processes to separate and purify ketones and glycols produced by microbial fermentation. In one or more embodiments, methods in accordance with the present disclosure may be used to recover organic fermentation products such as ketones and glycols from aqueous solutions having various concentrations of salt.

The use of fermentation processes in biorefineries is being used to develop renewable raw materials for industrial production of plastics and other fine chemicals. Scaling these processes up to commercially relevant scales presents a number of challenges from establishing optimum microbial growth conditions, in addition to the isolation of the pure biologically-derived products from complex mixtures of salts and organic materials obtained from fermentation tanks.

Methods in accordance with the present disclosure may utilize renewable feedstocks that are converted, by fermentation, to a number of commercially relevant products that are isolated from the off-gas and/or broth exiting the fermenter. Products in accordance with the present disclosure may include, for example, ketones, alcohols, and glycols, which are made using metabolic pathways harnessed by biotechnological processes. In one or more embodiments, fermentation processes may produce glycols and ketones in fermentation broths and/or off-gas streams. Compared to conventional process for the production of these chemicals, the compositions of the streams have a unique nature, particularly due to the presence of the target products, high concentrations of water, and the presence of salts in the fermented broth. As a result, fermented product streams contain impurities and by-products that are distinct from those typically associated with industrial chemical production. Methods in accordance with the present disclosure address these differences in the purification process.

Figure 1:
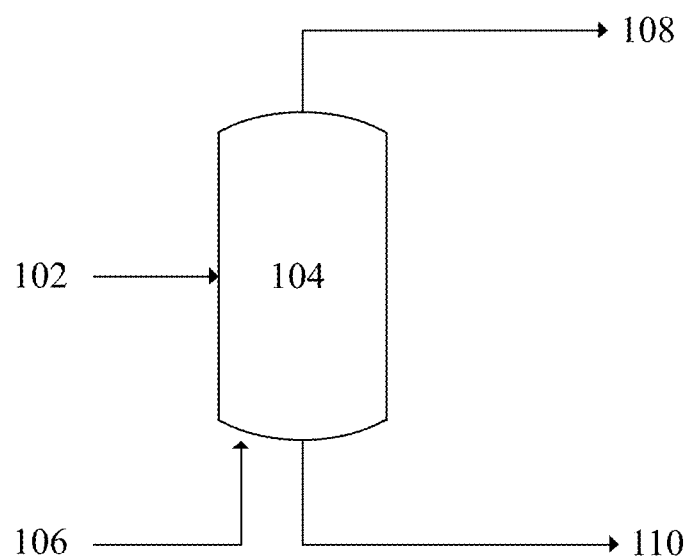
FIG. 1 is a flow diagram of a fermentation process in accordance with embodiments of the present disclosure.

With particular respect to FIG. 1, a simple fermentation setup is presented. A feedstock stream 102 is introduced into fermenter 104, which contains a selected media tailored for the particular microorganism being cultivated. For example, a feedstock stream 102 may contain water, sugar, salts, and various organic and inorganic nutrient mixtures. For aerobic fermentation, an air supply 106 may be introduced into the fermenter to provide an oxygen source. As fermentation progresses, an off-gas stream 108 may be generated containing incondensable gases, water, various ketones, aldehydes, and alcohols, and a number of trace contaminants that exits the fermenter. Fermented broth 110 may also be captured, which contains various concentrations of water, glycols, ketones, alcohols, salts, carboxylic acids, organic matter, and inorganic matter.

Methods in accordance with the present disclosure are directed to processes to separate and purify industrially-relevant compounds such as ketones and glycols produced during fermentation, which may be recovered in off-gas and fermented broth mixtures obtained from a fermenting vessel. Following recovery, the output streams may be treated separately. In some embodiments, methods include isolating volatile compounds from incondensable gases and other impurities through a number of gas separation technologies. Volatile compounds may then be processed further to recover and isolate organics such as ketones.

In one or more embodiments, fermented broth may be transferred from a fermenter to a fluid separation module where various purification technologies may isolate valuable products such as glycols, alcohols, and other components. In some embodiments, fermented broth may be pretreated prior to forwarding to the fluid separation module, using a number of techniques including sterilization, filtration, salt removal, and concentration. Volatiles in the fermented broth stream may be transferred to the gas separation module and combined with the off-gas products in other embodiments.

Methods in accordance with the present disclosure may include the use of fluid separation modules that are tailored to the separation of components from a fermented broth containing salts. The presence of salts in broth may complicate the use of distillation and other separation techniques, because such techniques may utilize the removal of water that can generate solids and other scales and/or may induce corrosion and other negative effects.

Off-Gas Separation and Ketone Recovery

In one or more embodiments, processes and systems in accordance with the present disclosure may include a module or series of modules for partitioning an off-gas stream received from a fermenter into its constituent components. Off-gas generated from a fermenter may contain large proportions of incondensable gases such as $O_2$, $N_2$, and $CO_2$. Gases $O_2$ and $N_2$ are often the return from an air supply injected into the fermenter, while $CO_2$ may be generated as a byproduct of microbial metabolism. As the off-gas product stream is processed, the removal of incondensable gases may be required to recover other valuable components from the product stream. In some embodiments, the off-gas stream may be processed into its constituents, for example, to separate and purify ketones from other components such as incondensable gases.

Off-Gas Separation Module

In one or more embodiments, processes and systems in accordance with the present disclosure may use absorption-based or condensation-based purification techniques to process fermenter off-gas (108 in FIG. 1). With particular respect to FIG. 2, off-gas separation technologies in accordance with the present disclosure may include an absorption module 200. Absorption separation may proceed by transferring an off-gas stream 202 from a fermenter (stream 108 in FIG. 1) to the bottom of an absorption column 204, which is then placed into contact with an absorption agent 206 (such as water) introduced at the top of a column. Separation of the product mixture occurs as incondensable gases 208 (such as $CO_2$, $N_2$, and $O_2$), which have limited affinity for the absorption agent, travel through and exit the column. The remaining product stream 210 exiting the column 204 contains soluble components from the gaseous feed 202 that may include water, ketones, other species of interest, and small quantities of incondensable gases. There are many suitable candidates for the absorption agent 206, such as water if the ketone has a low molecular weight.

Ketone Recuperation Module

The soluble components 210 obtained from the absorption column may include oxygenates, ketones, alcohols and other oxygenates, trace amounts of glycol, and acids, which are expected to be in a liquid mixture with absorbent as well as a very small quantity of incondensable gases. There are a variety of methods by which the ketones may be recovered from the diluted solution of soluble components 210, including for example distillation, evaporation, liquid-liquid extraction, pervaporation, etc. In one or more embodiments, the soluble components 210 may be forwarded to distillation column such as that discussed below with respect to FIG. 3.

Figure 2:
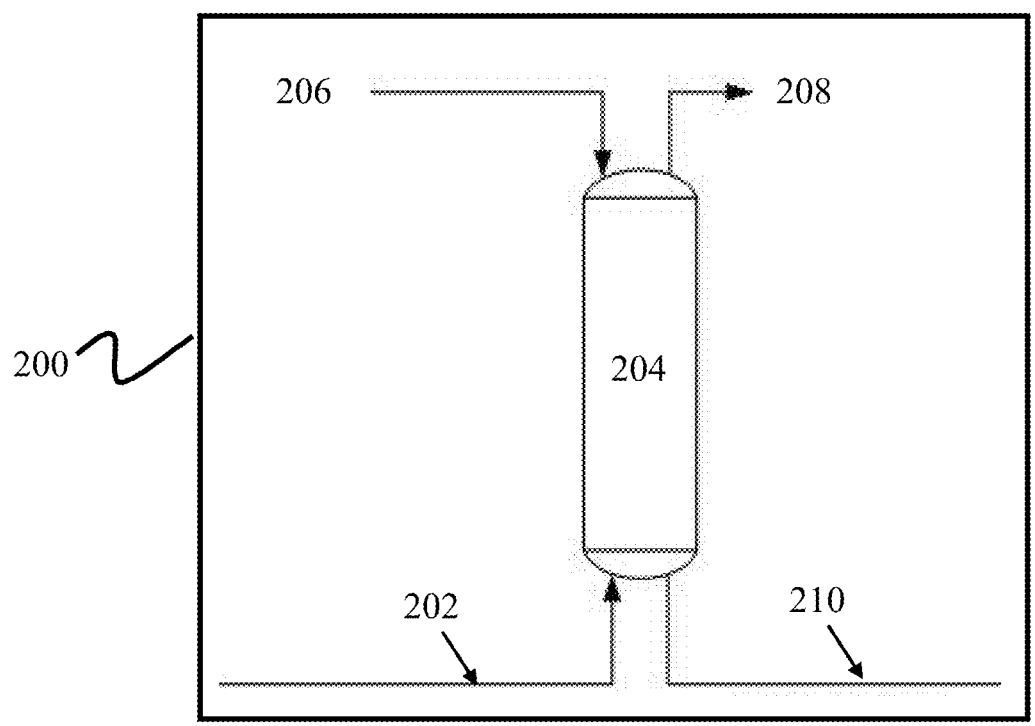
FIG. 2 is a flow diagram of a column absorption-based purification of fermenter off-gas in accordance with embodiments of the present disclosure.
Figure 3:
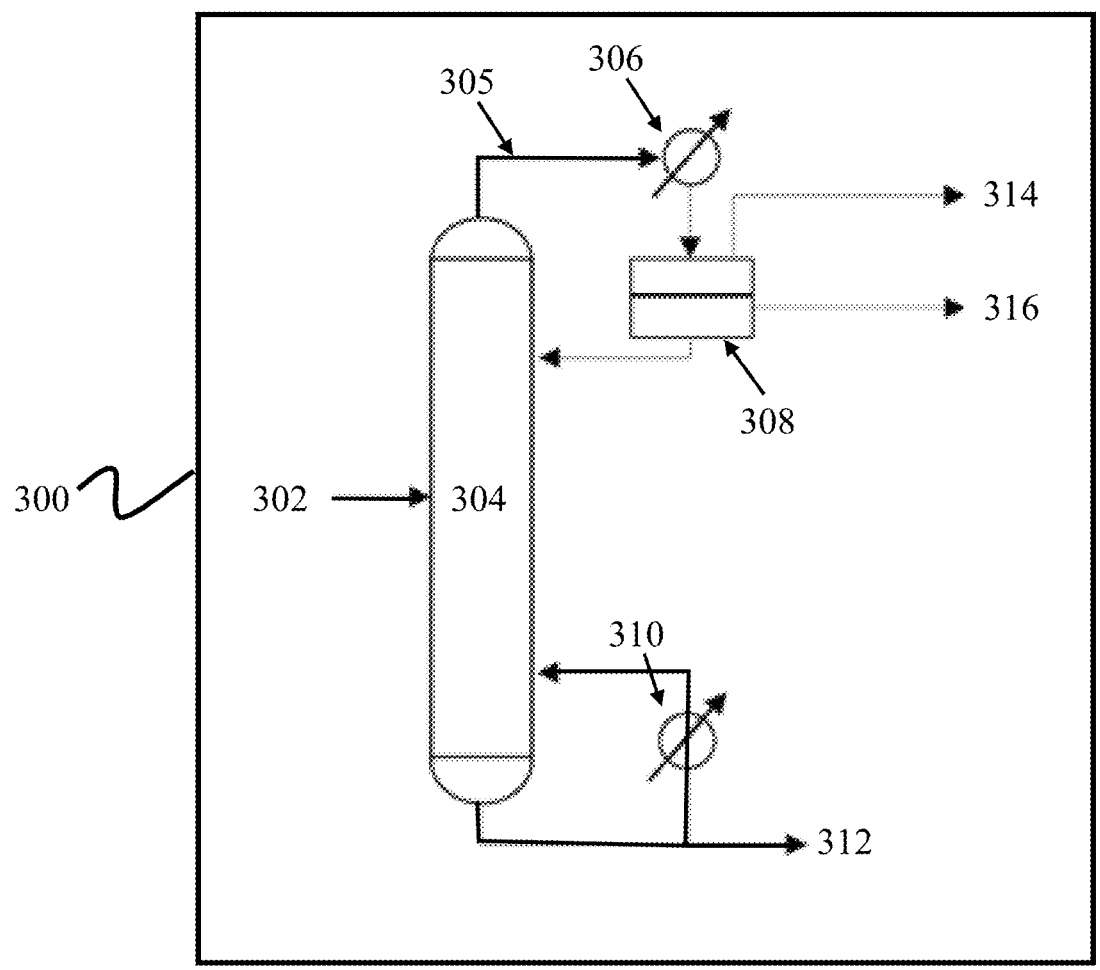
FIG. 3 is a flow diagram of a distillation process in accordance with embodiments of the present disclosure.

With particular respect to FIG. 3, an embodiment of a ketone recuperation module 300 is shown. In this example, the liquid stream 302 coming from an off-gas separation module (stream 210 in FIG. 2, for example), which may contain a mixture of solvent, ketones, alcohols, water, acids, and trace amounts of glycols and incondensable gases, is fed into a distillation column 304, wherein the non-volatile (and often aqueous) component leaves as a bottom stream 312. The bottom stream 312 may contain mixtures of water, alcohols, ketones and other oxygenates, acids, and/or glycols in various concentrations. The overhead stream 305 from distillation column 304 may be cooled upon exiting the column, using a heat exchanger 306, for example. In some embodiments, condenser 306 may be followed by a reflux tank 308 to separate incondensable gases 314 (such as carbon dioxide, nitrogen, and oxygen) from ketones and other volatile components in stream 316. Part of the non-volatile components in flux 316 may be returned to the overhead of distillation column 304 for additional reflux in some embodiments. In one or more embodiments, ketone 316 can also be recovered in a side stream from column 304, below a pasteurization region.

The bottoms 312 of the ketone recovery column 304, which may contain the solvent (such as water), acids, and glycols, may be sent to wastewater treatment or may be treated to remove the contaminants from the solvent, which may be recirculated back to the absorption column 304 in some embodiments. Treatment may be done by distillation, evaporation, adsorption, liquid-liquid extraction or other unit operation known by the state of the art. The non-condensable gases 314 from the overhead stream 305 may optionally be cycled to an absorption module, discussed with respect to FIG. 2, in order to recover residual losses of the ketone in some embodiments. Thus, in one or more embodiments, technologies used to process off-gas components may include distillation coupled with partial condensation as discussed at 306 in FIG. 3.

Fluid Separation and Glycol Recovery

In one or more embodiments, processes and systems in accordance with the present disclosure may include one or more fluid separation modules that partition fluid streams obtained from a fermenter into their various constituent components. In some embodiments, fluid separation modules may be used to isolate ketones, glycols, and other industrially-relevant compounds from fermentation processes.

Fluid Separation Modules

Processes and systems in accordance with the present disclosure may contain one or more fluid separation modules to separate a fermented broth stream obtained from a fermenter into its various constituent components. Fermented broths have a number of characteristics and components that are unique when contrasted with other industrial processes used to generate feedstocks. In addition to water and compounds of interest, a fermented broth stream may contain solids, salts, minerals, carboxylic acids, phenolic compounds, proteins, and unconverted sugars. Examples of solids includes precipitated sugars such as arabinose, mannose, glucose and its oligomers, xylose and its oligomers, and others; various organics such as succinic acid and precipitated lignin; and biomass including live and dead bacteria, yeast, and other microbes.

In fermentation broths, salts are often used to create favorable conditions for microorganisms, and are often present in downstream processes in noticeable concentrations. Salt precipitation can become an issue, particularly through the formation of insoluble salts or by water evaporation. Precipitated salts can cause flow issues in addition to heat transfer surface fouling, which can result in time and financial expense to address. However, it is also envisioned that in one or more other embodiments, such salt removal is not necessary, and glycol is recovered from a salt-containing fermented broth. In such cases, care should be taken such that the water concentration of the broth is maintained above the solubility limit of the salts, in order to avoid salt precipitation. Moreover, materials that contact fermentation streams should be selected with consideration to the types of salts in the production streams. For example, some salts such as chlorides, are known by their high corrosion potential, and equipment handling product streams with these salts should be resistant to corrosion.

Methods in accordance with the present disclosure may be used to remove products of interest from product streams containing a range of salt concentrations using one or more fluid separation modules that may operate by a number of techniques that may include distillation, reactive distillation (RD), reactive extraction (RE), thin-film evaporation (TFE), short path evaporation (SPE), continuous chromatography, and batch chromatography. Further, in one or more embodiments, methods of separating components from a fermented broth having a high concentration of salts may involve the use of a separating agent that enhances the separation of products of interest such as ketones and glycols from a fermented broth. A number of possible techniques are discussed in turn as follows.

Distillation Series

Methods of glycol recovery from aqueous solutions may include distillation by one or more distillation columns. When salts are present in the broth, their precipitation in process equipment, either chemically or as a result of water evaporation, may cause flow issues in the process, surface fouling, and often lead to downtime to address these issues. Salts are required for creating favorable fermentation conditions for microorganisms, and are often present in downstream processes in non-negligible concentrations.

In one or more embodiments, a distillation series may be used to purify glycol and other target compounds, following the removal or reduction of salt concentration using a salt removal module or other pretreatment module, discussed below. In some embodiments, a product stream leaving a salt removal module may be separated using a distillation series having two or more distillation columns to recover organics such as glycols. With particular respect to FIG. 5, a sample arrangement of distillation columns in a distillation module 500 is shown. As a product stream 502 (which may include, for example, water, lighter organics, glycol, and heavier organics) enters a first distillation column 504, water and lighter organics may be removed as an overhead stream 506. The bottom stream 508 contains compounds such as glycol and other heavies, which are transferred to a second distillation column 510 in the series. Glycol and other compounds exit the second column 510 as an overhead stream 512, while heavies are ejected as bottom stream 514.

Reactive Distillation

Reactive distillation is a process intensification technique, in which a chemical reaction and a distillation occur in a single equipment. In one or more embodiments, fluid separation modules may include the use of reactive distillation to separate polyols such as glycol from a fermented broth by reacting the polyol with a separating agent having a carbonyl species (e.g., aldehydes or ketones) that reacts with polyols to form the corresponding acetal. Acetals in accordance with the present disclosure include ketals or acetals prepared from the reaction of carbonyl species including respectively ketones or aldehydes with alcohols and include compounds historically referred to as ketals and acetals. Further, acetals in accordance with the present disclosure include cyclic acetals such as dioxolanes and dioxanes. Acetal species such as dioxolanes are often more volatile than the corresponding polyol and have a reduced capacity for hydrogen bonding, allowing the acetal to be separated from the solution in the reactive distillation column. It is also envisioned that "acetal" as used herein may represent a heterogeneous mixture of acetals generated from multiple carbonyl species present in a product stream, including acetals generated from both ketones and aldehydes.

Figure 6:
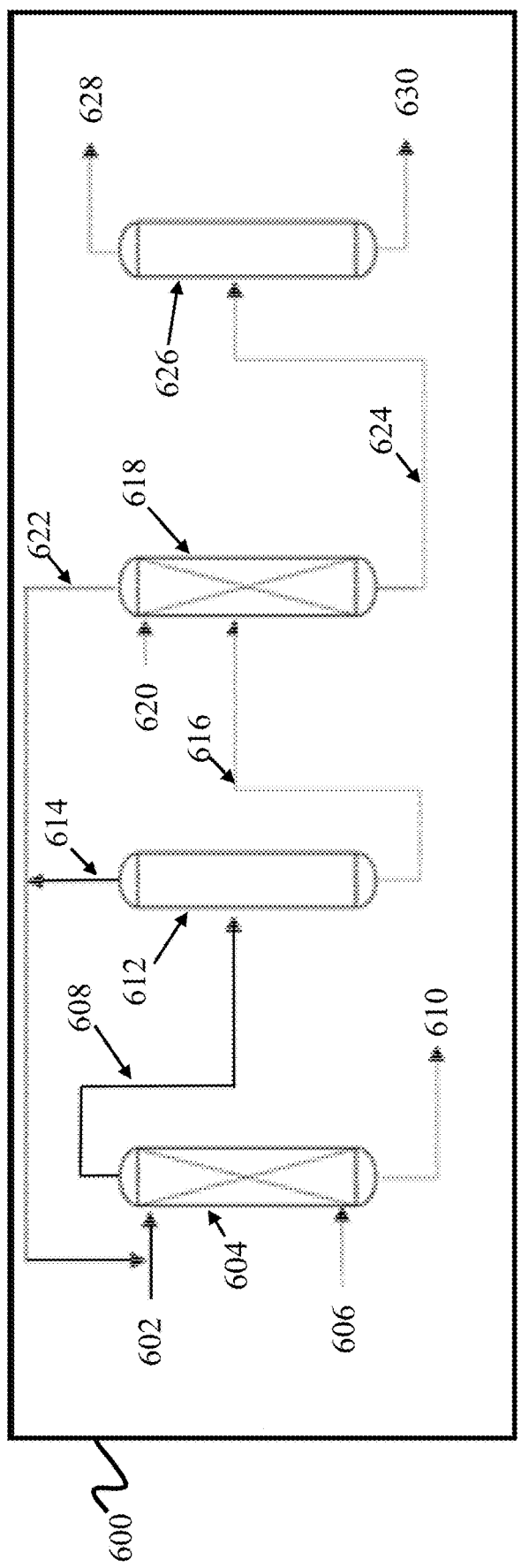
FIG. 6 is a flow diagram of a reactive distillation process in accordance with embodiments of the present disclosure.

With particular respect to FIG. 6, an embodiment of a fluid separation module 600 incorporating a reactive distillation column is shown. In the embodiment, a broth stream 602 (which has been clarified and optionally concentrated) is transferred to reactive distillation column 604, while separating agent 606 (a carbonyl species, for example) is fed into the column 604 at another location. In one or more embodiments, glycol present in the broth stream 602 reacts with the separating agent 606 in the column 604, transforming glycol to the corresponding acetal form by means of a reaction with the separating agent in the presence of a catalyst. In the case of the reaction of glycol and a carbonyl species, a cyclic acetal is formed. For example, monoethyleneglycol reacts with formaldehyde forming 1,3-dioxolane and water, while and monoethyleneglycol reacts with acetone giving 2,2-dimethyl-1,3-dioxolane. The acetal forms of glycol are more volatile than water, and may be distilled as an overhead stream 608 together, often with some concentration of residual carbonyl species. Conversion to acetals may occur in the presence of a catalyst in some embodiments. Catalysts may include mineral acids such as hydrochloric acid, or ion exchange resins. Acetal-forming reactions are equilibrium reactions and stoichiometric excesses of carbonyl species may be used to drive the reaction to higher conversion rates in some embodiments.

In one or more embodiments, a portion of water may leave the reactive distillation column 604 with acetal obtained as overheads 608, due to the formation of a minimum-boiling azeotrope between acetal and water. Nevertheless, the majority of the water may remain at the bottom of the column 604 to maximize the solubility of the salts in the remaining broth, which may exit the column as bottom stream 610. The reactive distillation column overheads 608 are passed to a second distillation column 612, where the unreacted separating agent (i.e., a carbonyl species such as aldehyde or ketone), is recovered as an overhead stream 614 and recycled back to the first column 604.

The bottoms 616 from the second column 612 are sent to a third distillation column 618 (hydrolysis column), where water 620 is added to hydrolyze the acetal to obtain the corresponding glycol. The bottom stream 624 of the hydrolysis column 618 is a water/glycol mixture, and this is ultimately sent to a final distillation column 626 to remove water as an overhead stream 628, while glycol is obtained at 630. In one or more embodiments, ketones or aldehydes obtained from a fermented broth as a co-product of the fermentation may be used as separating agent 606 used for reactive distillation.

In some embodiments, flow stream 630 may be sent to a final distillation column where the heavy compounds are withdrawn in a bottom stream, while purified glycol is obtained as an overhead stream. In some embodiments, purified glycol may be collected and stored following cooling by a heat exchanger. While glycol is shown as a representative polyol in this example, it is envisioned that the process may be adapted to capture other polyol species containing two or more available alcohol groups and/or two or more carbon atoms, 1, 3 propylene glycol, for example.

Reactive Extraction

In one or more embodiments, reactive extraction may be used as a process intensification technique, in which a chemical reaction and a solvent extraction occur in a single combined process to separate glycols and other organics. Similar to reactive distillation discussed above, reactive extraction operates by modifying the solubility and volatility of glycols by reacting them with a separating agent to generate the corresponding acetal or cyclic acetal. Further, a solvent is introduced into the reactive distillation column, which extracts hydrophobic and nonpolar species from the aqueous fermented clarified broth stream if a pretreatment module is used. Reactive extraction utilizes the change in affinity of the converted glycol (dioxolane, for example) for the organic solvent phase, aiding separation. Hydrolysis of the converted glycol then regenerates the glycol product downstream.

Figure 7:
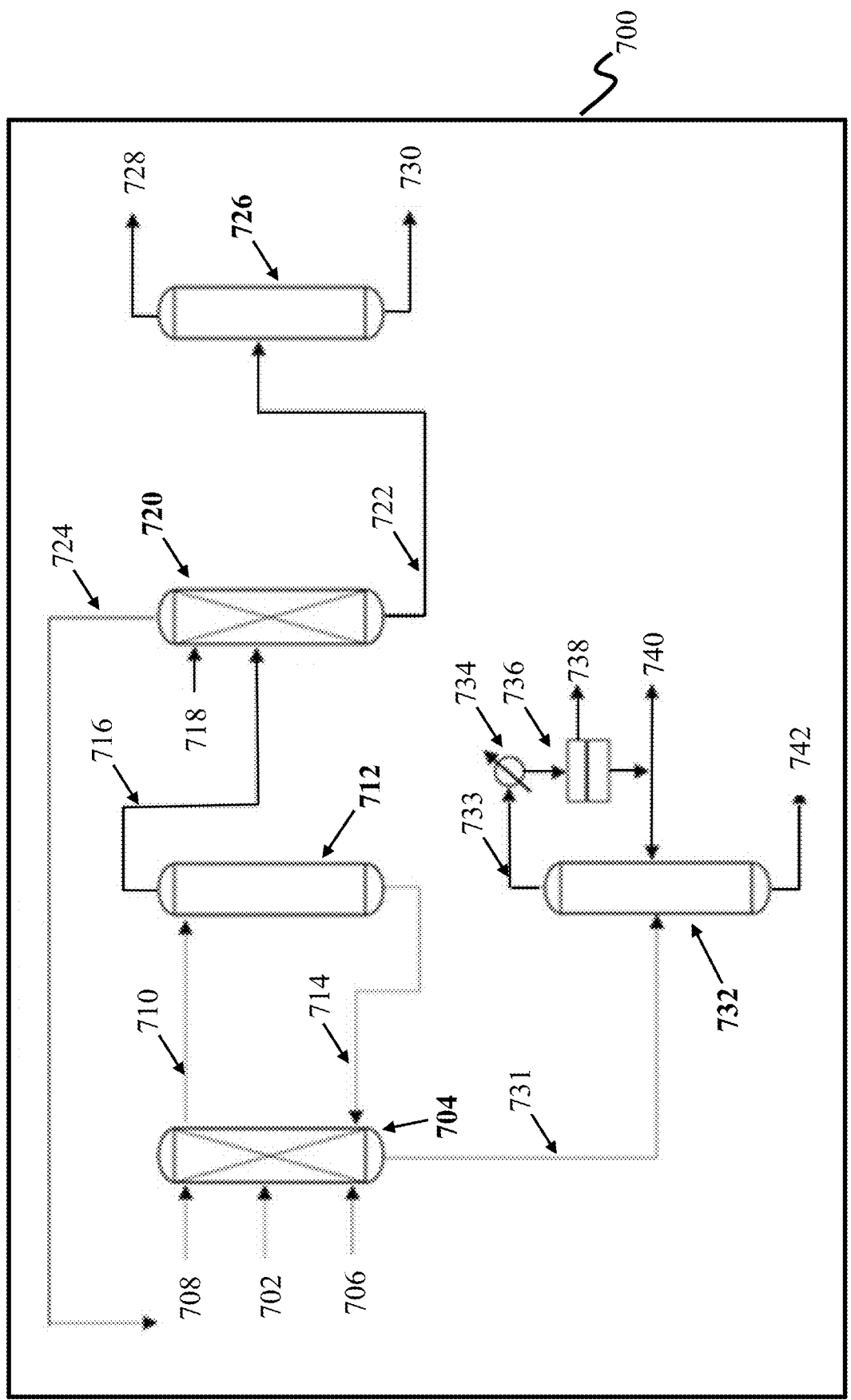
FIG. 7 is a flow diagram of a reactive extraction process in accordance with embodiments of the present disclosure.

With particular respect to FIG. 7, a reactive extraction module 700 is shown. A fermented broth stream 702 (which has been clarified and/or concentrated in some embodiments) is transferred to reactive extraction column 704. The reactive extraction is then initiated by converting glycol to an acetal using separating agent 706, such as aldehyde or ketone, which is combined with the broth 702 in reactive extraction column 704. Thereafter, instead of distilling the acetal from the aqueous mixture as described with respect to FIG. 6, the dioxolane is extracted using a solvent 708, which is transferred from column 704 as stream 710 containing reactant, acetal, solvent, and a fraction of water.

The solvent-rich phase 710, containing the acetal, is then withdrawn and sent to a distillation column 712 to recover the solvent as stream 714. In tower 712, acetal is recovered as an overhead stream 716 and the solvent removed at the bottoms 714 is recycled back to the reactive extraction column 704. The acetal flow is sent to a reactive distillation column 720, called hydrolysis column, where water 718 is added to revert the acetal back to glycol, which leaves as bottom stream 722 as a mixture with water. The overhead stream 724 contains mainly reverted separating agent, such as an aldehyde or ketone, which may be recycled back to the reactive extraction column 704. The bottoms 722 of this hydrolysis column is, once again, a water and glycol mixture, and this is ultimately sent to a final distillation column 726 to generate an overhead stream 728 containing water and a bottom stream 730 containing glycol. In one or more embodiments, flow stream 730 may be sent to a final distillation column where heavy compounds are withdrawn in a bottom stream, while glycol is obtained in an overhead stream. In some embodiments, purified glycol may be collected and stored following cooling by a heat exchanger. One advantage of configurations such as that described is that ketones already present in the process as a co-product of the fermentation, may be used as a separating agent 706 for reactive extraction.

The solvent may be chosen in order to promote recovery of the acetal in the organic phase. In one or more embodiments, organic solvents may include toluene, ethylbenzene, o-xylene, and the like. The aqueous phase 731 from the reactive extraction column 704 may contain water, salts, sugars, separating agent, acetals, and solvent in some embodiments. After leaving reactive extraction column 704, aqueous phase 731 may be transferred to distillation column 732 equipped with a decanter 736. The separating agent, acetal, and solvent are recovered in the organic phase of the decanter 736 as stream 738 and may be recycled to the solvent recovery column 712 in some embodiments. One advantage of this configuration is that ketones are already present in the process as a co-product of the fermentation, may be used as separating agent 706 used for reactive extraction. For example, bottoms 731 from the reactive extraction column 704 may be sent to distillation column 732 in order to recover solvents, reactants, and to eliminate residual water. For example, bottoms 731 may be separated into an overhead stream 733, which may be cooled using heat exchanger 734 and passed to decanter 736 to separate the overhead stream 733 into a fraction 738 containing organics such as aldehydes, ketones, acetals, and solvent, and a water fraction 740. Water and other heavies that exit column 732 as the bottoms may be recovered as stream 742.

Evaporator Modules

In one or more embodiments, a fluid separation module may incorporate one or more thin film evaporators and/or short path evaporators to recover organics and water, while salts and heavier components such as sugars are separated. In some embodiments, a fermented clarified broth stream may be concentrated in a concentration module, and transferred to a first stage evaporator to recover a stream enriched in glycol and water. A second stage evaporator, working at a lower pressure may also be added to the system to help to recover glycol from the liquid of the first evaporator. In this case, the evaporated flow from the second evaporator is condensed and pumped back to the first evaporator and the liquid, which now contains a higher salt concentration, is purged from the system.

The thin-film evaporators prevent salts from fermented broths from sticking to heated surfaces. This technology also has several advantages such as short residence time, high heat transfer coefficients due to turbulent flow, ability to handle high solids concentrations and viscous materials, and less product decomposition, resulting in higher yields. Constructively, a thin film evaporator is formed from a sealed vessel equipped with a heating jacket. The feed flows down the evaporator wall by gravity, with or without the assistance of mechanical wipers, and forms a thin film that covers the evaporating surface and drives heavies down to a bottom exit. Due to the heating and applied vacuum, the volatile components are evaporated and then liquefied in an external condenser. The components that are not evaporated are pumped out or discharged.

In some embodiments, short path evaporators can be used for glycol recovery. Also known as molecular distiller, a short path evaporator (SPE) is very similar to thin-film evaporator, except that it contains a condenser concentrically fixed within the apparatus. A SPE generally consists of two concentric cylindrical bodies, in which one act as an evaporation surface and the other acts as a condensation surface. The feed of liquid material to be concentrated/distillated falls through the heated wall and partially vaporizes. As steam is generated, it encounters the cold wall and condenses.

In some embodiments, a separating agent such as a salt entrainer is introduced to the broth medium to maintain salts in the liquid phase, during thin film evaporation and short path evaporation for example, while lighter organics such as ketones and glycols are evaporated and collected by the thin film evaporator. Entrainers in accordance with the present disclosure are viscous products that are usually of a higher molecular weight than the target ketone or glycol compound. Due to the viscous nature of the chemicals, feedstock sugars or glycerol can be used as salt entrainers that maintain salts in the liquid phase, while volatile components and water vaporize from solution. In one or more embodiments, salt entrainers (such as glycerol in this example) may be added to a fermented clarified broth at an excess concentration, such that salts are kept in the liquid phase and entrained to the bottom of the evaporator.

Figure 8:
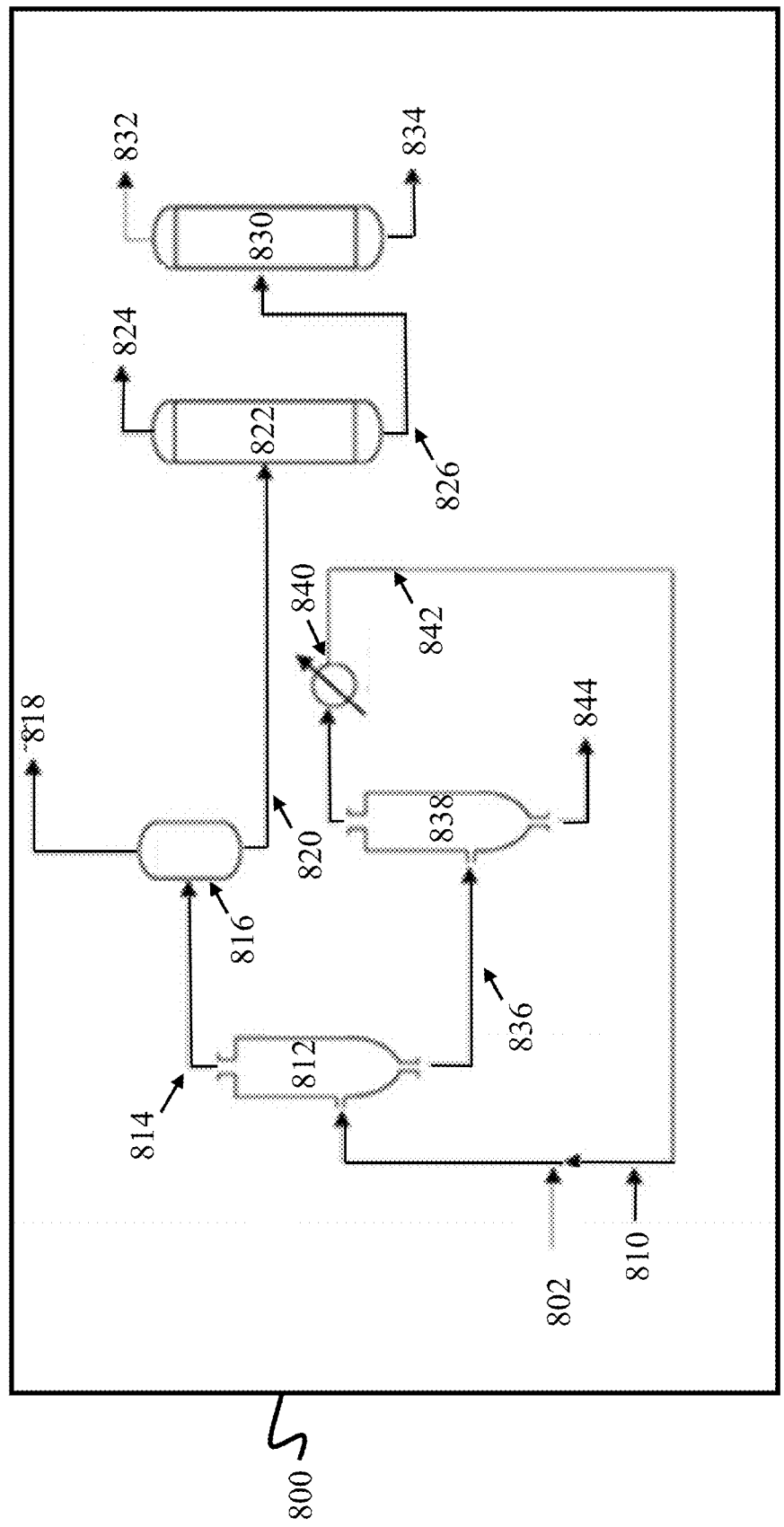
FIG. 8 is a flow diagram of a thin-film evaporation process in accordance with embodiments of the present disclosure.

With particular respect to FIG. 8, an embodiment of a fluid separation module utilizing an arrangement of thin film evaporators is shown. A fermented broth 802 (which has been clarified and optionally concentrated in some embodiments) may be combined with a salt entrainer from stream 810 and transferred to a thin-film evaporator 812 to evaporate off the glycol, light components, and water, while the salts are entrained by the separating agent, and carried to the bottom exit of the evaporator at 836 along with other components such as salts and sugars. The separating agent/entrainer also prevents the salts from sticking to the walls of the evaporator and enhances the glycol recuperation in the evaporated stream.

If the separating agent/entrainer still contains a considerable quantity of glycol, a second evaporator 838, working at a lower pressure may be added to recover glycol from the liquid coming from the first evaporator as stream 836. In this case, the evaporated flow 842 from the second evaporator 838, which is rich in the salt entrainer but also contains glycol, is passed through condenser 840 and pumped back to the first evaporator 812. Any unrecycled separating agent leaves as bottom of the second thin film evaporator as stream 844. Stream 844 is often rich in salt entrainer and salts, and may be considered a waste stream in some embodiments. In fermentation broths containing high concentrations of sugars and/or glycerol, the amount of makeup 810 needed for recycling the entrainer to stream 842 may be negligible to none.

The distillate product 814 from the first evaporator 812 in any of the above embodiments may be enriched in glycol, light organics, salt entrainer, and water, which is then sent to a partial condenser 816 where the glycol is condensed as stream 820, while water, light organics, and some glycol exit as overhead stream 818. Stream 820 containing glycol, salt entrainer, light organics, and water may then be transferred to a distillation series containing columns 822 and 830 to produce the purified glycol. For example, stream 820 is transferred to column 822 which is separated to overhead 824 containing water and light organics, and bottom stream 826 containing glycol, heavy organics, and salt entrainer. Stream 826 is then polished in column 830 to generate a glycol product stream 832 and separated heavies and entrainer fraction 834. In an alternative configuration, the distillate coming from the first evaporator 812 is completely condensed in the condenser 816 and after is sent directly to a distillation series such as columns 822 and 830. Here, the first distillation column 822 removes water at the top product 824 and its bottom product 826 is sent to the second column 830, where glycol is recovered at the overhead 832 and the bottom 834 containing the heavies is purged from the process.

While the examples presented include entrainer, it is also envisioned that fluid separation modules incorporating thin film evaporation may be performed without separating agents, or by using endogenous separating agents such as a sugars by modifying the concentration of sugars applied to and leaving the fermenter.

Chromatography Modules

Fluid separation modules in accordance with the present disclosure may include one or more chromatographic modules. Chromatographic methods in accordance with the present disclosure may include the separation of solutes in a mixture based on differences in migration rates through a two phase system. Although it may be used as an analytical technique for identifying components in a mixture, chromatography may be used on a continuous large scale to separate and purify the products in various syntheses.

In batch chromatography, a pulse of the feed mixture is injected into a column packed with an adsorbent and a continuous flow of a solvent passes continuously through the column. Due to the difference of affinity of the adsorbent to the various solutes, they migrate through the column at distinct speeds and are thus separated. However, because batch operation is often inefficient, requiring large amounts of solvent and making an inefficient use of the column throughout separation, continuous chromatographic systems have been developed to provide more efficient operation resulting in higher productivities.

In one or more embodiments, the chromatography module may be configured to perform continuous chromatography. The large-scale production of chromatographic products may require continuous and autonomous systems that offer higher efficiency and lower solvent consumption than batch units. The simulated moving bed is an established continuous chromatographic technique used in several fields. Several other continuous systems have also been developed such as True Moving Bed (TMB), simulated moving bed (SMB), pseudo-SMB, intermittent-SMB, supercritical SMB, Gradient SMB, POWERFEED™, MODICON™, variable external streams systems, VARICOL™, Multi-Feed, and others.

In one or more embodiments, a fermented broth may be processed by a salt removal module, and passed through a chromatography module to generate at least one fraction containing purified glycol and at least one fraction containing other fermentation co-products. In some embodiments, operation of the chromatography module may be carried out batch-wise or by a continuous process.

Salt Removal Module

Fluid separation modules in accordance with the present disclosure may include processing a fermented broth to obtain glycols and other species of interest by sequential treatment by a salt removal module to removing salts and other ionic species, followed by treatment with a distillation series to enrich for the target compound.

Salt removal modules in accordance with the present disclosure may include a number of technologies such as filtration, precipitation, ion exchange, and electrodialysis. Salt removal pretreatment modules can be applied separately or combined, depending on the characteristics of the broth. As used herein, "salt removal" may include complete removal of the salt concentration from a liquid stream, or removal of a portion of the salt concentration.

In one or more embodiments, glycols and other species of interest may be purified from a fermented clarified broth by removing salts using a salt removal module followed by separation of glycols using a fluid separation module. In some embodiments, methods may include purifying glycols and other species of interest by removing at least a portion of salts using a pretreatment module Filtration Filtration technologies such as nanofiltration, may be used to remove dissolved salts. Nanofiltration can separate multivalent ions from a liquid stream with considerable efficiencies.

In one or more embodiments, salt removal methods may be used to remove salts from the fermented broth. With particular respect to FIG. 9 a salt removal module incorporating a series of techniques is shown. The fermented clarified broth stream 902 passes through a nanofiltration (NF) 904 generating a NF retentate 906. Once NF retentate is removed the stream is then transferred to an ion exchange section 908 which captures charged species and produces a reduced salt stream 910.

Precipitation Module

Other techniques that may be used to reduce salt concentration include precipitation followed by a solid separation step. Precipitation may refer to chemical precipitation or evaporative precipitation (crystallization, for example). In chemical precipitation, a compound foreign to the process is introduced, changing the solubility and causing salts to precipitate. In evaporative precipitation or crystallization, the solvent is removed beyond the solubility limits of salts, causing a portion of salts to crystallize and precipitate. Precipitated salts may then be removed by a number of techniques including decantation, centrifugation, filtration, or other known form of solids separation.

Ion Exchange

In one or more embodiments, salt removal methods may include using ion exchange to remove a portion of salt from a fermented clarified broth stream prior to passage of the fluid through a fluid separation module. In ion exchange technology, a fermented clarified broth passes through one or more ion exchange units, where ions of opposite charges are attracted and retained on the ion exchange resins. The removed ions are replaced by other ions. The resins may be either cationic, anionic, or mixed-charged. Ion exchangers may be used in series, and may include cationic and anionic exchanger sections. Depending on the characteristics of the fermented broth, multiple ion exchange units may be used, optionally with an evaporation step to concentrate the clarified solution between the series. After drawing ions from a stream the resin progressively saturates, and the ion exchange units need to be regenerated using chemicals appropriate for the charge of the unit, including acids and bases, which generates an effluent. In one particular embodiment, ion exchange module may be preceded by a nanofiltration unit. This technology is effective to partially remove non monovalent ions and can relieve the ion charges imposed to the ion exchange modules.

Electrodialysis

In one or more embodiments, salt removal may include one or more electrodialysis cells. Electrodialysis is a technique in which ions are transported across an electrically-driven ion exchange membrane. Electrodialysis membranes may be either cation or anion-selective, allowing only same charged species to pass through, and rejecting opposing charges. In an electrodialysis cell stack, several membranes of alternating selectivity are placed to maximize the retention of ions. Electrodialysis is also useful in that it does not require a regeneration step. In one particular embodiment, electrodialysis module may be preceded by a nanofiltration unit. This technology is effective to partially remove non monovalent ions and can relieve the ion charges imposed to the electrodialysis modules.

Figure 5:
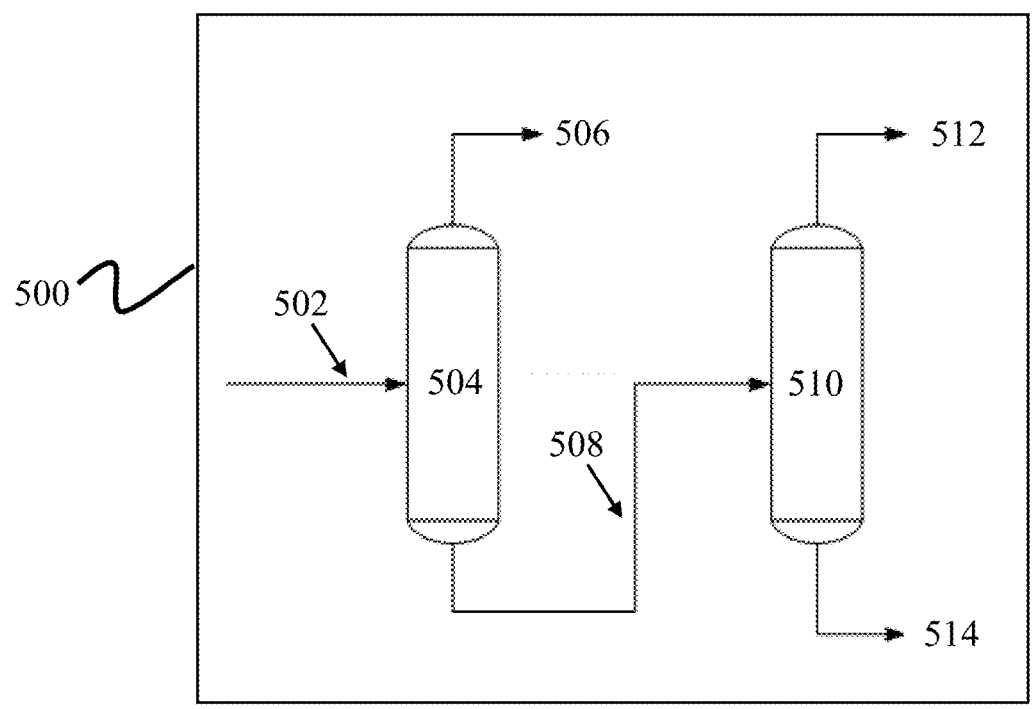
FIG. 5 is a flow diagram of a distillation process in accordance with embodiments of the present disclosure.

Following the removal of salt by a salt treatment module, glycol and other species of interest may be isolated using a distillation column or distillation series such as that discussed with respect to FIG. 5 and the accompanying text.

Salt removal in accordance with the present disclosure may also include nanofiltration followed by ion exchange in some embodiments, or by precipitation and/or nanofiltration followed by ion exchange in other embodiments. In yet other embodiments, precipitation and/or nanofiltration may be performed and followed by electrodialysis. In other embodiments, salt removal may be done by precipitation and/or nanofiltration followed by ion exchange and/or electrodialysis. In addition, in all the non-limiting embodiments previously described, a water removal step may be performed between modules, such as evaporation or membrane separation (reverse osmosis). While a number of examples are presented for clarity, it is envisioned that the modular nature of the techniques discussed above permit any combination of pretreatment modules and salt removal to be performed prior to and/or following the use of fluid separation modules without departing from the scope of the instant disclosure.

Pretreatment Processing of Fermented Broth

In one or more embodiments, a fermented broth must undergo a number of pretreatments prior to processing by a fluid separation module. Pretreatment methods in accordance with the present disclosure may include reducing solids and salt content of a fermented broth.

Pretreatment Modules

In one or more embodiments, a fermented broth from the bottom stream from a fermenter (i.e., broth 110 from fermenter 104 in FIG. 1) is pretreated prior to purification of glycols and other components in downstream processing in fluid separation modules. Pretreatment modules may be placed in line prior to a fluid separation module in some embodiments. Following processing by a pretreatment module and a fluid separation module, the generated product stream may be sent to one or more distillation columns or similar separation technology to isolate purified glycols and other species of interest.

In some embodiments, pretreatment of a fermented broth may include sterilization and/or clarification to remove solids, biomass, and organic matter. For example, the fermentation broth may contain solids, salts, minerals, carboxylic acids, aldehydes, phenolic compounds, furans, ketones, glycols, alcohols, proteins, and unconverted sugars. Examples of solids include precipitated sugars (arabinose, mannose, glucose and its oligomers, xylose and its oligomers, etc.), succinic acid, precipitated lignin, and biomass (bacteria or yeast cells). Thus, pretreatment of a fermented broth may include centrifugation to remove cells and other precipitated solids alone or followed by one or more filtration techniques including microfiltration, ultrafiltration, and nanofiltration to remove unconverted sugars, large molecules, and cell debris. In one or more embodiments, the clarification may be done without centrifugation and using one or more filtration techniques.

In one or more embodiments, cells and other solids obtained from clarification techniques such as centrifugation may be washed to recover the glycol contained in the cell moisture. In other embodiment, centrifugation is followed by microfiltration and/or ultrafiltration and/or nanofiltration to remove unconverted sugars, cell debris, and other solubilized large molecules. In some embodiments, clarification is done by a microfiltration followed by ultrafiltration and/or nanofiltration.

The term "fermented clarified broth" which will hereinafter be used means the fermented product whose cells and other solids have been partially or completely removed.

Figure 4:
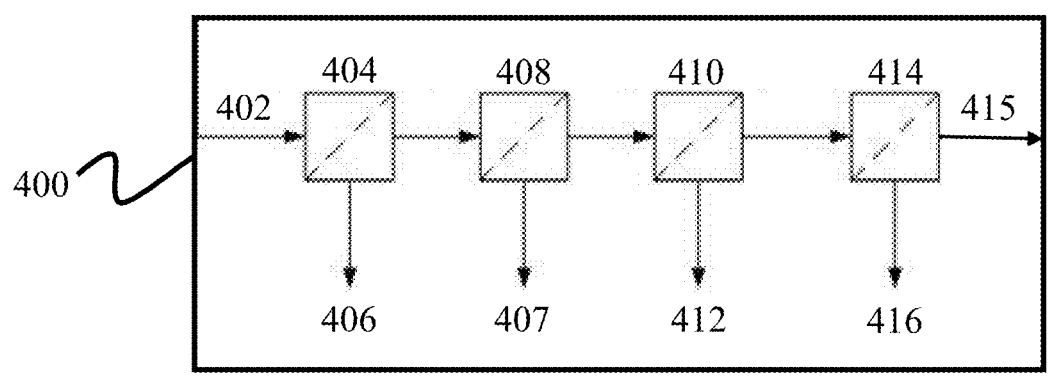
FIG. 4 is a flow diagram of a pretreatment process of a fermented broth in accordance with embodiments of the present disclosure.

With particular respect to FIG. 4 a pretreatment module incorporating a series of pretreatment techniques is shown. As fermented broth 402 leaves the fermenter, the broth is centrifuged at 404 to remove solids and biomass 406. The liquid fraction continues to microfiltration 408 for further clarification, removing additional solids and biomass 407, before passaging to ultrafiltration (UF) 410, generating UF retentate 412 before passing to nanofiltration (NF) 414 and generating a NF retentate (416) and a fermented clarified broth 415.

Light Organics Separation Module

In one or more embodiments, processes and systems in accordance with the present disclosure may include a ketone and light organics separation module to recover remaining ketone and light organics that may be present in the fermented clarified broth. Methods for ketone and light organics separation from the fermented clarified broth may include distillation by one or more distillation columns, and/or evaporation in an evaporator system.

Figure 10:
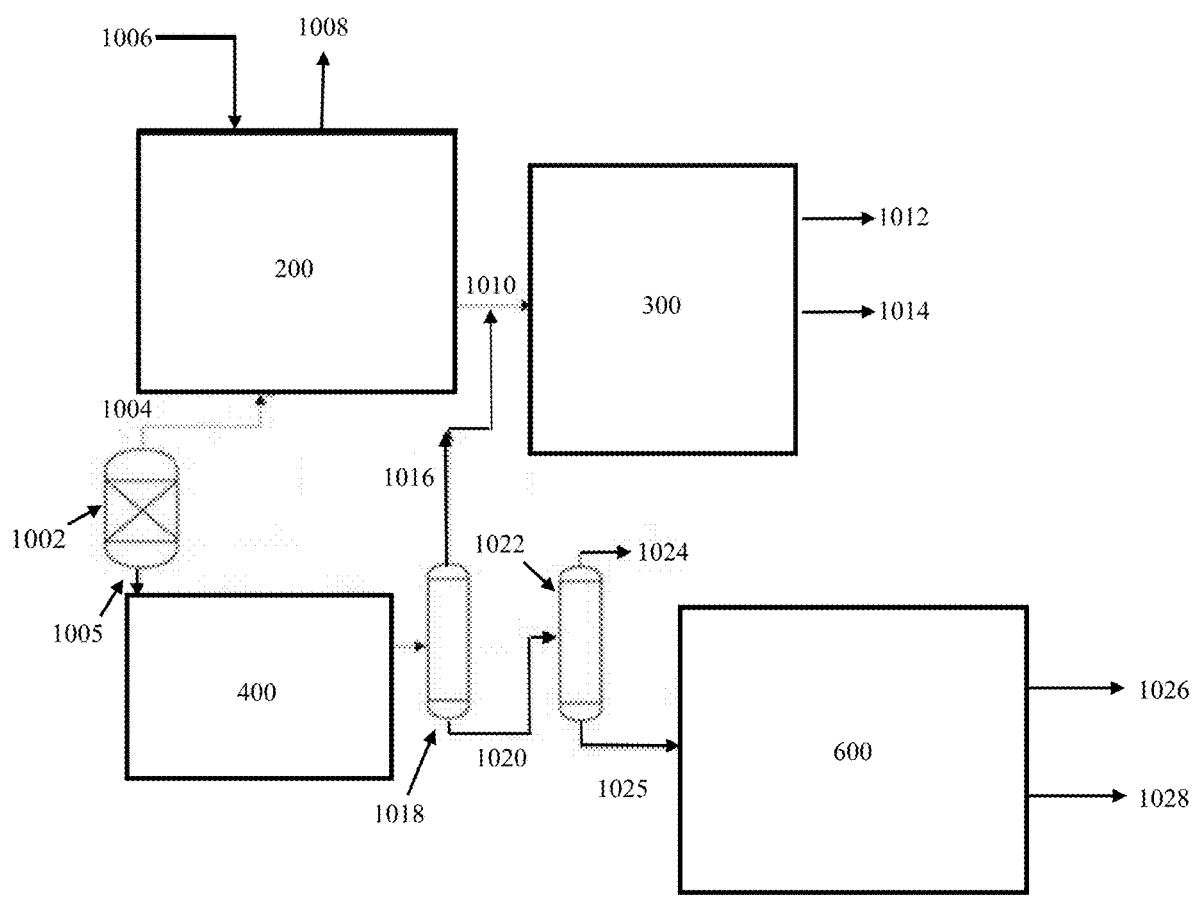
FIG. 10 is a flow diagram of a fermentation purification process using a reactive distillation process in accordance with embodiments of the present disclosure.

In one or more embodiments, one or more distillation columns may be used to separate ketone and other lighter compounds from the fermented clarified broth, following the removal of solids and cells using a pretreatment module, discussed above. In some embodiments, a product stream leaving the pretreatment module may be separated using a distillation series having one or more distillation columns to recover ketone and light organics such as aldehydes and alcohols. As an example, with particular respect to FIG. 10, the fermented broth leaves the fermenter 1002 as stream 1005, which may then be pretreated using a pretreatment module 400, which may remove cells, solids and a portion of solids and salts from stream 1005, which is then transferred to distillation column 1018. Distillation column 1018 may remove volatiles such as dissolved incondensable gases, water, ketones and other organics, which may then be routed as stream 1016 and combined with the stream 1010 entering the distillation module 300 and processed accordingly.

Concentration Module

In one or more embodiments, a concentration module may include a distillation series that may include a first distillation column that concentrates organics and other compounds in the fermented clarified broth. A fraction of the water removed from the concentrated broth may exit an overhead stream from the column, while the concentration of salts in the remaining concentrated stream remains below the saturation point, minimizing or eliminating possible salt precipitation.

The concentration step is not limited to a distillation column, other kinds of technologies may be used such as multiple effect columns or evaporators, including thermal vapor recompression, mechanical vapor recompression evaporators or a combination of multiple effect and thermal vapor recompression, or mechanical vapor recompression.

Additional Treatment Processing of Products from Fermented Broth

Methods in accordance with the present disclosure may involve the use of color and odor removal modules to polish product-containing streams obtained from a fluid separation module or even between the steps described inside a fluid separation module. In some embodiments, color and odor removal modules may be placed in line within a fluid separation module prior to final stage separation of glycol and other products, such as prior to passing a product-containing stream to a distillation column or distillation series.

Color and Odor Removal Modules

In one or more embodiments, methods in accordance with the present disclosure may incorporate color and odor removal modules to polish streams containing products of interest. Compounds such as residual sugars, aldehydes, ketones, phenolic compounds, furan derivatives and others may introduce coloring that can negatively affect product quality, such as when product streams are heated in the downstream separation processes.

In one or more embodiments, one or more color and odor removal modules may be added to the processes in accordance with the present disclosure. Removal of coloring and UV absorbing impurities in accordance with the present disclosure may occur at any point in the purification process to obtain target compounds such as ketones and glycols, including after pretreatment of a fermented broth by centrifugation and/or filtration, prior to, after or between the unit operations of the fluid separation processes, or combinations thereof. For example, the use of color and odor removal modules such as activated carbon beds and/or hydrogenation reactor and/or ultraviolet (UV) treatments may be placed prior to or following a fluid separation module, including distillation, reactive distillation (RD), reactive extraction (RE), thin-film evaporation (TFE), short path evaporation (SPE), continuous chromatography, and batch chromatography.

In some embodiments, color and odor removal modules may include treating a fermented clarified broth stream using one or more techniques such as contacting the stream with an activated carbon bed, a hydrogenation catalytic reactor, or exposing the stream to UV radiation. In some embodiments, an activated carbon bed may adsorb organics and other compounds responsible for color, while in a hydrogenation catalytic reactor a stream of hydrogen is used to hydrogenate color precursors such as unsaturated organics and other color precursors. In some embodiments, hydrogenation catalytic reactor and treatment with UV radiation are placed before the final distillations to separate compounds that may be formed.

Applications: Integrated Gas and Fluid Separation

In this section, embodiments of methods and systems to separate gases and fluids obtained from a fermentation process are provided.

Example 1—Reactive Distillation

In a first example, a process in accordance with the present disclosure is used to isolate ketones and glycols from microbial fermentation using reactive distillation. With particular respect to FIG. 10, fermenter 1002 generates an off-gas stream 1004 that is transferred to absorption module 200, described with respect to FIG. 2 and the accompanying text, which utilizes input water 1006 to absorb ketones and compounds of interest that exit the module as stream 1010, while allowing incondensable gases 1008 (including $CO_2$, $N_2$, and $O_2$) to exit the column. Stream 1010 is then transferred to ketone recuperation module 300, described with respect to FIG. 3 and the accompanying text, which generates stream 1012 containing the remaining incondensable gases (which may be recycled back to module 200 in some embodiments), and stream 1014 enriched in ketone.

The fermented broth leaves the fermenter 1002 as stream 1005, which may then be pretreated using a pretreatment module 400, described in FIG. 4 and the accompanying text, which may remove cells, and a portion of solids and salts from stream 1005, which is then transferred to distillation column 1018, which is a light organics separation module. Distillation column 1018 may remove volatiles such as dissolved incondensable gases, water, ketones and other organics, which may then be routed as stream 1016 and combined with the stream 1010 entering the ketone recuperation module 300 and processed accordingly.

The bottoms 1020 from column 1018 containing glycols and other products of interest are transferred to another distillation column 1022 such as a multiple effect distillation column, which concentrates stream 1020 by removing a water fraction 1024 as overheads, and transferring the bottoms 1025 to reactive distillation module 600, described with respect to FIG. 6 and the accompanying text. Following the module 600, a water stream 1026 is generated in addition to the glycol enriched stream 1028.

In an alternative configuration, the glycol enriched stream 1028 from the bottom of the dehydration column 1022 is sent to a hydrogenation reactor where a catalyst uses a small flow of oxygen to hydrogenate color contaminants. After the hydrogenation, glycol is sent to a distillation column such as column 604 represented in module 600 (FIG. 6).

Activated carbon can also be used to reduce color or odor. In one or more embodiments, the glycol enriched stream 1025 from the bottom of the dehydration column 1022 is sent to an activated carbon bed, where the color and UV absorbers contaminants are adsorbed. In some embodiments, glycol enriched stream 1028 from module 600 may be sent to an activated carbon bed, where the color and UV absorbing contaminants are absorbed. The purified glycol may then be cooled and sent to storage.

While glycol is shown as a representative polyol in this example, it is envisioned that the process may be adapted to capture other polyol species containing two or more available alcohol groups and two or more carbon atoms, monoethylene glycol or propylene glycol, for example.

Example 2—Reactive Extraction

In another example, a process in accordance with the present disclosure is used to isolate ketones and glycols from microbial fermentation using reactive extraction. The reactive extraction process is similar to the reactive distillation process, but differs in the manner in which the acetal is separated from the broth. Particularly, a reactant is added to a reactive extraction column, which converts glycol into acetal. A solvent is also added in the reactive extraction column, and the acetal and part of the unreacted reactant are removed from this column by means of extraction. Solvents used may have partial miscibility with water, but may be selected such that acetal has a higher affinity for the solvent to aid partitioning away from the aqueous phase. Possible solvents are toluene, ethylbenzene and o-xylene. The solvent counter-currently contacts a fermented clarified broth in the column, extracting the dioxolane simultaneously while the reaction takes place. In some embodiments, the organic phase (solvent, acetal, reactant and other contaminants) leaves the column as a top stream, while the aqueous phase (water, solubilized salts and sugars, and part of the organics) remain at the bottom of the column.

Figure 11:
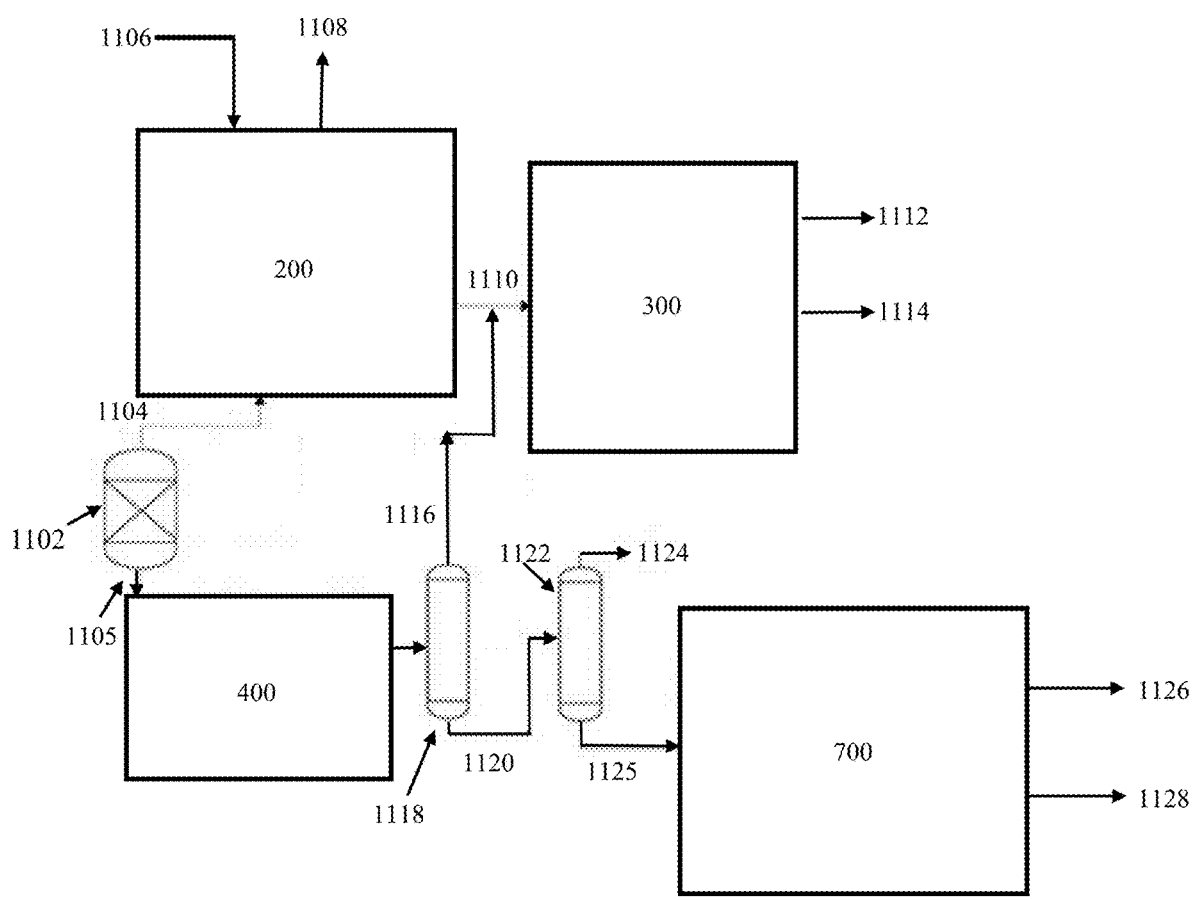
FIG. 11 is a flow diagram of a fermentation purification process using a reactive extraction process in accordance with embodiments of the present disclosure.

With particular respect to FIG. 11, fermenter 1102 generates an off-gas stream 1104 that is transferred to absorption module 200, described with respect to FIG. 2 and the accompanying text, which utilizes input water 1106 to absorb ketones and compounds of interest that exit the module as stream 1110, while allowing incondensable gases 1108 to exit the column. Stream 1110 is then transferred to ketone recuperations module 300, described with respect to FIG. 3 and the accompanying text, which generates stream 1112 containing the remaining incondensable gases (which may be recycled back to module 200 in some embodiments), and stream 1114 enriched in ketone.

The fermented broth leaves the fermenter 1102 as stream 1105, which may then be pretreated using a pretreatment module 400, described in FIG. 4 and the accompanying text, which may remove cells, solids and a portion of salts from stream 1105, which is then transferred to distillation column 1118, which is a light organics separation module. Distillation column 1118 may remove volatiles such as water, ketones, other light organics, and residual incondensable gases, which may then be routed as stream 1116 and combined with the stream 1110 entering the ketone recovery module 300 and processed accordingly.

The bottoms 1120 from column 1118 containing glycols and other products of interest are transferred to distillation column 1122, which concentrates stream 1120 by removing a water fraction 1124 as overheads, and transferring the bottoms 1125 to reactive extraction module 700, described with respect to FIG. 7 and the accompanying text. In one or more embodiments, distillation column 1122 may be multiple effect distillation columns or an evaporator series to concentrate stream 1120. Following the module 700, a water stream 1126 is generated in addition to the glycol enriched stream 1128.

In an alternative configuration, the glycol enriched stream 1125 from the bottom of the dehydration column 1122 is sent to a hydrogenation reactor where a catalyst uses a small flow of hydrogen to hydrogenate color and UV absorbers contaminants. After the hydrogenation, glycol may then be sent to module 700. Activated carbon can also be used to reduce color and odor. In another embodiment, the glycol enriched stream 1125 from the bottom of the dehydration column 1122 is sent to an activated carbon bed, where the color and UV absorbers contaminants are adsorbed. In other embodiments, glycol enriched stream 1128 from module 700 may be sent to an activated carbon bed, where the color and UV absorbing contaminants are absorbed. Then purified glycol is cooled and send to storage.

While glycol is shown as a representative polyol in this example, it is envisioned that the process may be adapted to capture other polyol species containing two or more available alcohol groups and two or more carbon atoms, monoethylene, monoethylene glycol or propylene glycol, for example.

Example 3—Thin Film Evaporation

In the next example, a process in accordance with the present disclosure is used to isolate ketones and glycols from microbial fermentation using thin film evaporation. With particular respect to FIG. 12, fermenter 1202 generates an off-gas stream 1204 that is transferred to absorption module 200, described with respect to FIG. 2 and the accompanying text, which utilizes input water 1206 to absorb ketones and compounds of interest that exit the module as stream 1210, while allowing incondensable gases 1208 to exit the module. Stream 1210 is then transferred to ketone recovery module 300, described with respect to FIG. 3 and the accompanying text, which generates stream 1212 containing the remaining incondensable gases, and stream 1214 enriched in ketone.

Fermented broth 1205 may be pretreated using a pretreatment module 400, described in FIG. 4 and the accompanying text, which may remove cells, solids, proteins, unconverted sugars and a portion of salts from stream 1205, which is then transferred to distillation column 1218, which is a light organics separation module. Distillation column 1218 may remove volatiles such as dissolved incondensable gases, water, ketones and other organics, which leave as an overhead stream that may be combined with the stream 1210 entering the ketone recovery module 300 and processed accordingly.

Bottom stream 1220 from distillation column 1218 containing glycols and other compounds of interest may then concentrated in a multi effect column system, here only represented by column 1222, which removes a water fraction 1224 as overheads, and a glycol concentrated stream 1225 at bottoms. Steam 1225 may be passed to thin-film evaporation module 800, described with respect to FIG. 8 and the accompanying text, which generates stream 1226 containing water, stream 1228 enriched in glycol and, if applicable, stream 1230 containing the entrainer and any residual salt.

Figure 12:
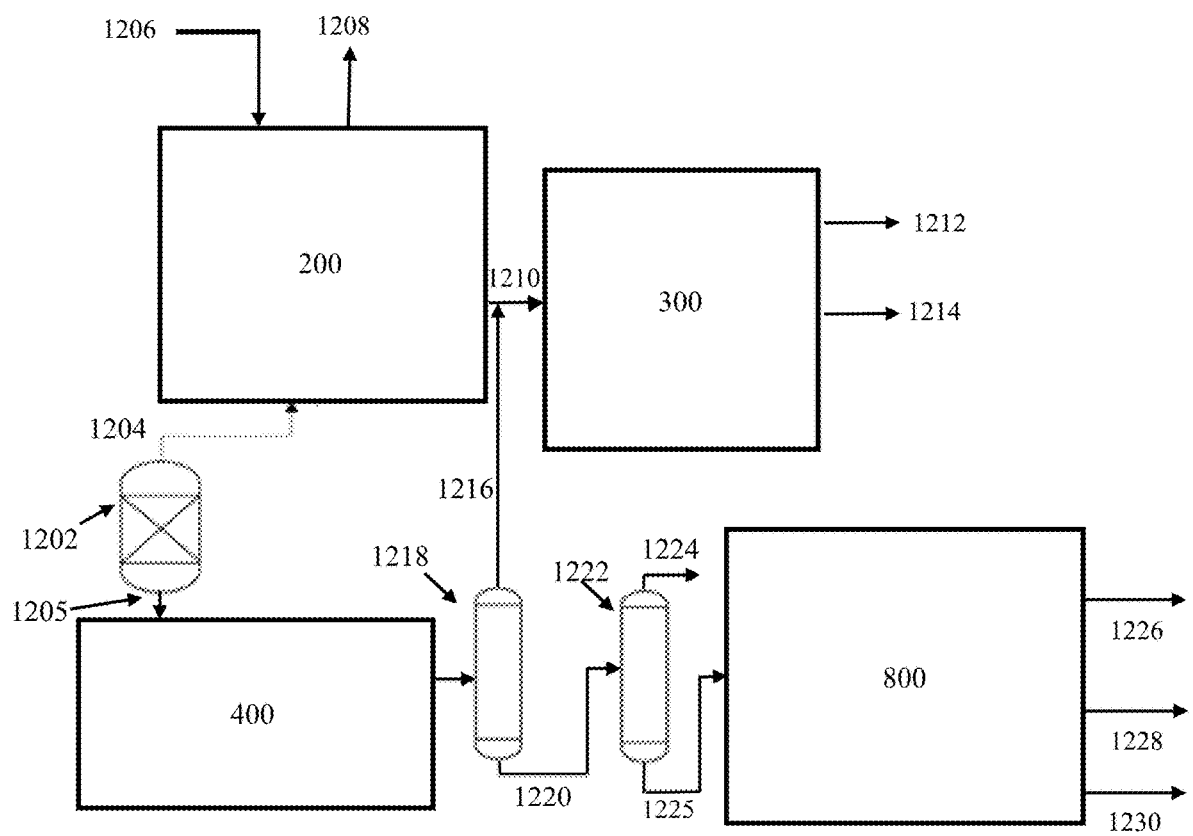
FIG. 12 is a flow diagram of a fermentation purification process using a thin-film evaporation process in accordance with embodiments of the present disclosure.

A treatment to remove color and UV absorbing impurities may also be added to the process in FIG. 12. An activated carbon bed or a hydrogenation reactor may be used for this purpose. In one embodiment, the glycol stream coming from the bottom of distillation column 1222 may be fed to a hydrogenation reactor where a catalyst uses a small flow of oxygen to hydrogenate color and UV absorbers contaminants. After the hydrogenation, the flow is sent to feed module 800. In another embodiment, the liquid glycol stream from the condenser 816, (with particular respect to FIG. 8) may be fed to a hydrogenation reactor where a catalyst uses a small flow of hydrogen to hydrogenate color and UV absorbers contaminants. After the hydrogenation, glycol may be routed back to distillation column 822 where the light components are removed as overheads 824 and the bottoms 826 are transferred to a to a second distillation column 830 where purified glycol is removed as 832 and sent to cooling exchanger and to storage. The heavies from the bottom may be sent to burning.

In another embodiment, the liquid glycol stream from condenser 816 is sent to an activated carbon bed, where the color and UV absorbers precursors are adsorbed. After treatment with carbon, and with particular respect to FIG. 8, glycol may be routed back to distillation column 822 where the light components are removed as overheads 824 and the bottoms 826 are transferred to a second distillation column 830 where purified glycol is removed as 832 and sent to cooling exchanger and to storage. The heavies from the bottom may be sent to burning. In other embodiments, glycol enriched stream 1228 from module 800 may be sent to an activated carbon bed, where the color and UV absorbing contaminants are absorbed. Then purified glycol is cooled and send to storage.

While glycol is shown as a representative polyol in this example, it is envisioned that the process may be adapted to capture other polyol species containing two or more available alcohol groups and two or more carbon atoms, monoethylene glycol or propylene glycol, for example.

Example 4—Salt Removal and Distillation

In the next example, a process in accordance with the present disclosure is used to isolate ketones and glycols from microbial fermentation using pretreatment/salt removal followed by distillation series.

Figure 13:
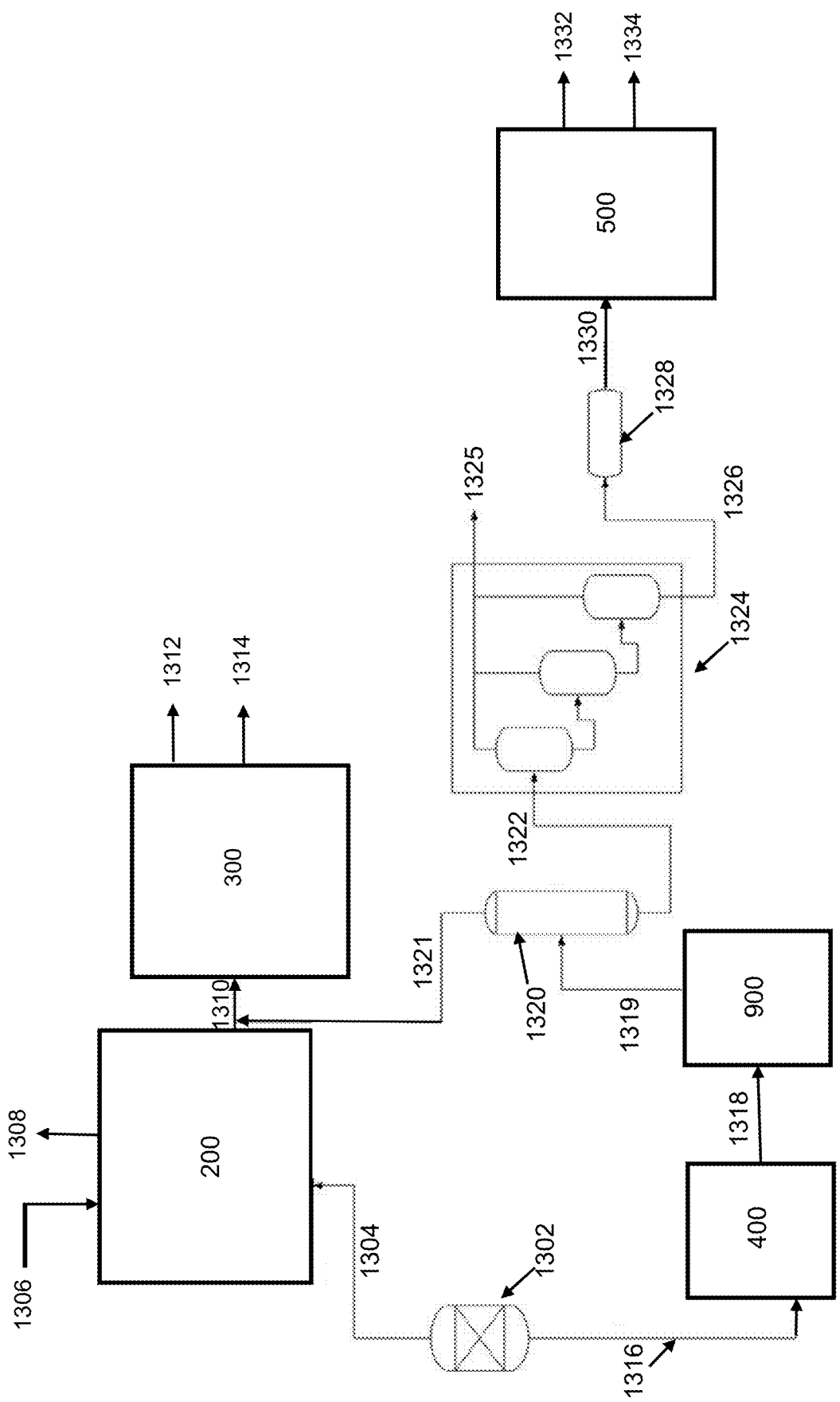
FIG. 13 is a flow diagram of a fermentation purification process using a pretreatment module in conjunction with a distillation module in accordance with embodiments of the present disclosure.

With particular respect to FIG. 13, fermenter 1302 generates an off-gas stream 1304 that is transferred to absorption module 200, described with respect to FIG. 2 and the accompanying text, which utilizes input water 1306 to absorb ketones and compounds of interest that exit the module as stream 1310, while allowing incondensable gases 1308 to exit the module. Stream 1310 is then transferred to ketone recuperation module 300, described with respect to FIG. 3 and the accompanying text, which generates stream 1312 containing the remaining incondensable gases (which may be recycled back to absorption module 200 in some embodiments to recover residual ketone), and stream 1314 enriched in ketone.

Fermented broth 1316 may be pretreated using a pretreatment module 400, which may remove cells and solids, and a portion and salts from stream 1316, generating stream 1318 after cells, solids and salt removal.

In the pretreatment module 400, the fermented broth coming from the fermenters is first clarified by the methods described above for solids, biomass and organic matter removal. Technologies that can be used are centrifugation and filtration (microfiltration, ultrafiltration and nanofiltration). Flocculating agents, may be added to increase the efficiency of the solid-liquid separation. In an embodiment, the clarification is done via centrifugation to remove the majority of cells and other precipitated solids. The solids may be washed to recover the glycol from the cells moisture, following a diafiltration procedure. A microfiltration module may be used to remove residual cells debris and fine solid particles. Diafiltration may also be used to recover glycols from retentate. In another embodiment, only microfiltration is used to remove the cells and precipitated solids and water sources such as diafiltration water can be used to recover the glycol from the retentate. In other embodiment, an ultrafiltration module can be used to remove polysaccharides, proteins and cell debris, and other high molecular weight compounds.

Figure 9:
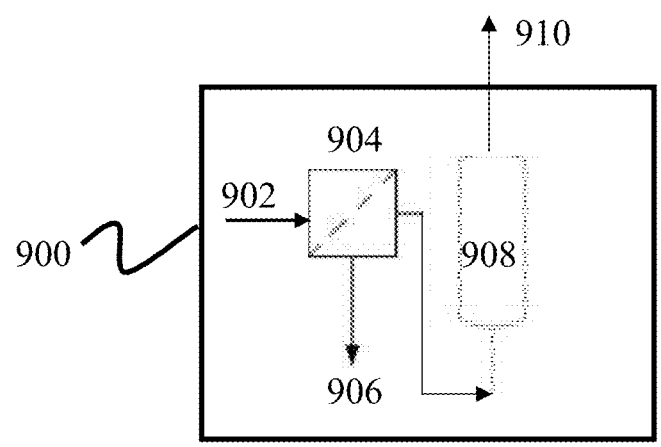
FIG. 9 is a flow diagram of a salt removal process of a fermented broth in accordance with embodiments of the present disclosure.

The clarified stream 1318 is then sent to the salt removal module 900, FIG. 9 and accompanying text, comprising a nanofiltration section to retain residual sugars, multivalent ions, and other high molecular weight compounds and an ion exchange section, passing through a series of cationic and anionic exchange modules, eliminating the dissolved salts from the stream. In another embodiment, an electrodialysis cell stacks may also be used to remove cations and anions.

Stream 1319, now having a very low concentration of salts, is then transferred to distillation column 1320, a light organics separation module, where volatiles such as ketones and other organics are separated as an overhead stream 1321 that may be combined with the stream 1310 entering the ketone recovery module 300 and processed accordingly.

The bottom stream 1322 from distillation column 1320 containing glycols and other products of interest may be passed through a multiple effect distillation columns 1324 (which may be a concentration module in some embodiments) to remove a combined stream 1325 containing water and other light organics and generate concentrated stream 1326. Several concentration technologies known in the art may be used in addition to or in place of 1324, including multiple effect evaporators or columns, thermal vapor recompression evaporators, or mechanical vapor recompression (MVR) evaporators, for example.

After the concentration by system 1324, an extra step of salt removal may be optionally required for polishing. The concentrated stream 1326 is then sent to an ion exchange module 1328, passing through a series of cationic and anionic exchange modules, which may virtually eliminate the dissolved salts from the stream. In some embodiments, electrodialysis membrane modules may be used to remove the cations and anions in addition to or in place of 1328. Following the ion exchange module 1328, stream 1328 may then be carried to distillation module 500, described with respect to FIG. 5 and the accompanying text, where the series of distillation columns generates stream 1334 enriched in glycol and a stream 1332 containing heavies and other residual components.

A treatment to remove color and UV absorbance impurities may also be added to the process in FIG. 13. A carbon activated bed or a hydrogenation reactor may be used for this purpose. In one or more embodiments, the glycol rich stream 1330 coming from ion exchange module 1328 may be fed to a hydrogenation reactor where a catalyst uses a small flow of hydrogen to hydrogenate color and UV absorbers contaminants. After the hydrogenation, stream 1330 may be redirected to distillation module 500, where the light components are removed and purified glycol is recovered as 1334. The heavies 1332 may be sent to burning in some embodiments. In some embodiments, glycol stream 1334 may be sent to an activated carbon bed for polishing to remove odor and color impurities. The purified glycol may then be cooled in an exchanger and sent to storage. The heavies from the bottom may be sent to burning.

In another embodiment the stream 1330 is sent to an activated carbon bed, where the color and UV absorbers precursors are adsorbed. The stream is then redirected to distillation module 500 to obtain the glycol stream 1334 and a heavies stream 1332.

While glycol is shown as a representative polyol in this example, it is envisioned that the process may be adapted to capture other polyol species containing two or more available alcohol groups, and two or more carbon atoms, monoethylene glycol or propylene glycol, for example.

Process Overview

Figure 14:
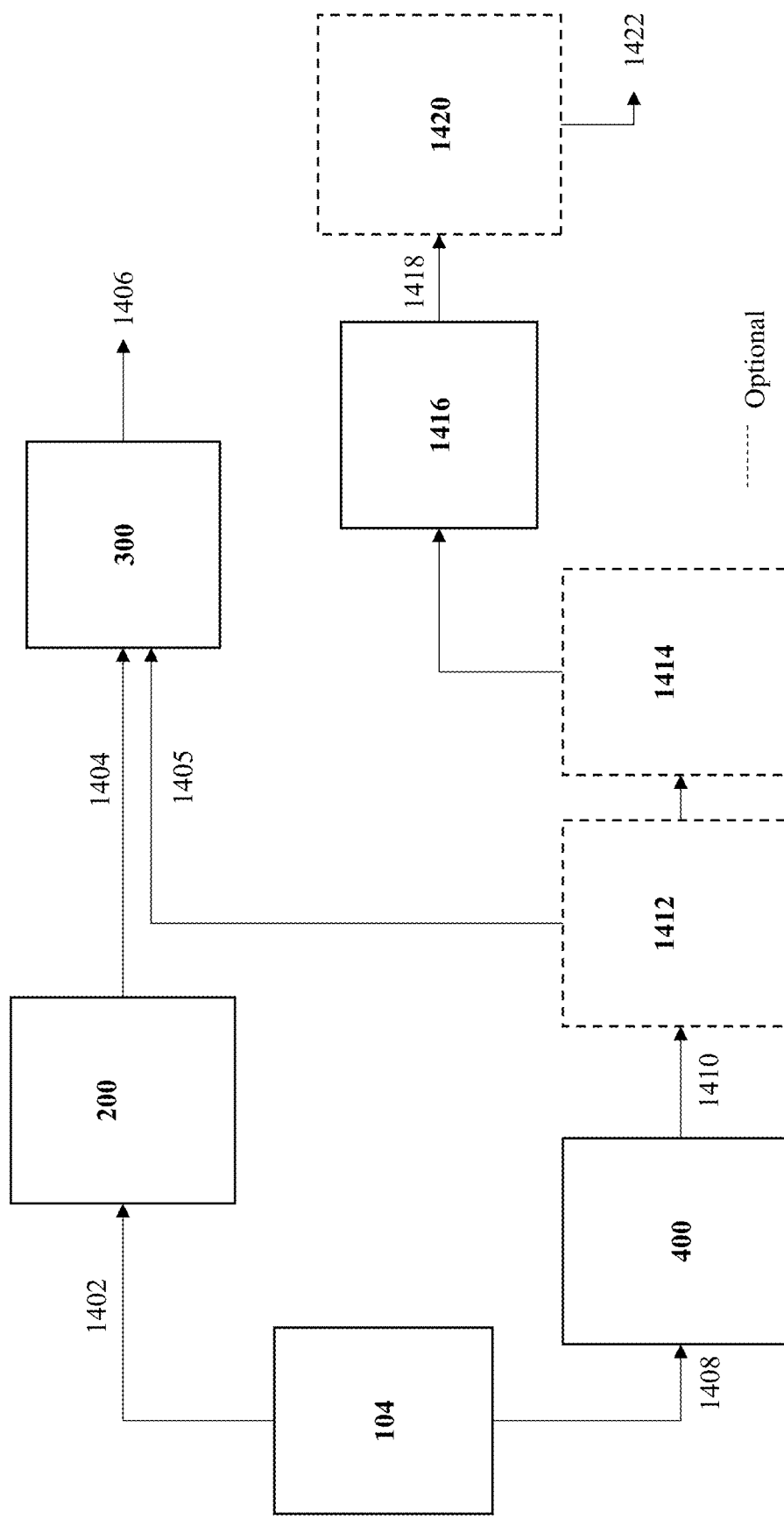
FIG. 14 is a flow diagram summarizing various module arrangements in accordance with embodiments of the present disclosure.

Methods in accordance with the present disclosure are directed to a modular approach for purifying select products from fermenter off-gas and fermented broth. With particular respect to FIG. 14, an overview of a generalized process flow is shown. Beginning with the initial fermentation chamber 104, off-gas 1402 may be directed to a gas separating module 200, which removes a portion of incondensable gases, producing stream 1404 containing ketones and other species of interest and potentially residual absorbing agent from gas separation module 200. Stream 1404 is then transferred to a ketone recuperation module 300 to isolate product stream 1406 containing ketones and/or target products.

The fermented broth obtained from fermenter 104 is redirected as stream 1408 to pretreatment module 400 where solids and cells are removed, generating fermented clarified broth stream 1410, and then transferred to fluid separation module 1416. In some embodiments, fermented clarified broth stream 1410 may be processed by a light organic separation module 1412 (indicated as optional by the dashed line) that may separate ketones and other light organics from the fermented clarified broth. Separated ketones may be redirected as stream 1405 to ketone recuperation module in some embodiments to isolate additional ketone. In some embodiments, fermented clarified broth stream 1410 may be transferred to a concentration module 1414 (indicated as optional by the dashed line)(with or without processing by light organic separation module 1412) to remove water and increase the concentration of ketones and target products in stream 1410.

Fermented clarified broth stream 1410 is transferred to fluid separation module 1416 where glycol and target products are separated as stream 1418 from other components in the fermented clarified broth by techniques discussed above such as reactive distillation, reactive extraction, evaporation (such as thin film evaporation and/or short path evaporation), and salt removal followed by distillation series. Product stream 1418 may then be post-treated by color and odor removal module 1420 (indicated as optional by the dashed line) in some embodiments generating purified product stream 1422. In some embodiments, color and odor removal module 1420 may be placed upstream of the final distillation columns in fluid separation module 1416, such as prior to exiting a reactive distillation module, or a reactive extraction module.

Modeling Simulation

In the following examples, a selected number of processes in accordance with the disclosure are simulated using Aspen Pius® (Aspen Technology, Inc., Burlington, Mass.).

Example 5: Reactive Distillation Simulation

Figure 15:
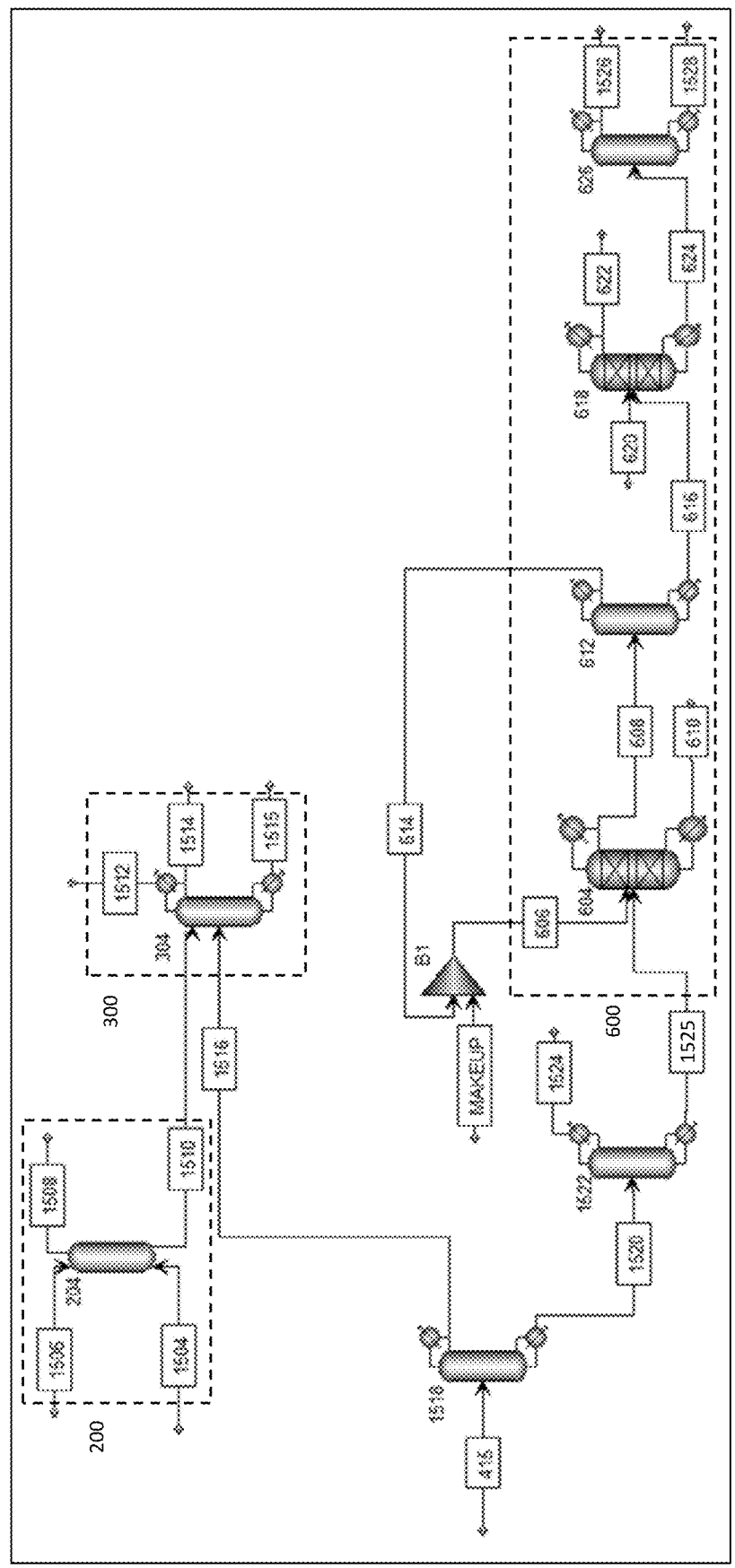
FIG. 15 is a flow diagram of a reactive distillation process in accordance with embodiments of the present disclosure.

In this example, a process in accordance with the present disclosure is used to isolate ketones and glycols from microbial fermentation broth using reactive distillation. With particular respect to FIG. 15, an off-gas stream 1504 from a fermenter is transferred to module 200 (dashed box), described in greater detail in FIG. 2, which contains column 204. In column 204, input water 1506 is employed to absorb ketones and compounds of interest, which exit as stream 1510. Incondensable gases, including $CO_2$, $N_2$, and $O_2$, leave as 1508.

Stream 1510 follows to the ketone recovery module 300 (dashed box), described in greater detail in FIG. 3 and the accompanying text, which contains column 304. In module 300, the majority of the ketone produced is recovered in stream 1514, while the remaining incondensable gases leave as 1512. In some embodiments, stream 1512 may be recycled back to column 204. The bottoms 1515 of the ketone recovery column 304, which may contain the solvent (such as water), acids, and glycols, may be sent to wastewater treatment or may be treated to remove the contaminants from the solvent, which may be recirculated back to the absorption column 204 in some embodiments.

Fermenters also produce a fermentation broth stream 415 that is directed to distillation column 1518 for removal of volatiles in some embodiments. Volatiles, including incondensable gases, water, ketones, and other organics, may be routed as stream 1516 and combined with 1510 to enter the ketone recovery module 304. In some embodiments, stream 415 may be pretreated using a pretreatment module (not shown, but such as that described in FIG. 4) to remove cells, insoluble solids, and salts prior to transfer.

The bottoms 1520 from column 1518, containing glycols and other products of interest, are transferred to another distillation step including column 1522 for partial removal of water. This can be accomplished by single or multiple effect distillation columns, or by a series of evaporators, depending on the feasibility of removing water without significant loss of products; in this example, one column was sufficient.

Optionally, as described above, after the concentration step, the glycol enriched stream 1525 from the bottom of 1522 may be sent to a hydrogenation reactor (not shown) where a catalyst uses a small flow of oxygen to hydrogenate color contaminants and UV absorbers. Subsequently, after optional hydrogenation, glycol rich stream 606 may be sent to a reactive distillation module 600 (dashed box) described in greater detail in FIG. 6 and the accompanying text. In one or more embodiments, stream 1525 is sent to an activated carbon bed, which is also capable of reducing color and odor. Removal of color and UV absorbers contaminants from glycol enriched stream 1525 may also be performed in an activated carbon bed following module 600.

In this example, however, the hydrogenation step was not performed, and bottoms 1525 followed directly to reactive distillation column 604 in module 600. Stream 606 includes carbonyl species that are introduced into column 604, which are then reacted with the glycol to form an acetal. Unreacted carbonyl, as well as acetal and other light components, were obtained in the top of column 604, exiting as stream 608. The bottoms 610, which may be considered a waste stream in some embodiments, include small quantity of unreacted glycol and other heavies.

Stream 608 is sent to an intermediate distillation step, performed by column 612 where the carbonyl species are separated as the top stream 614 of the column, while the rest of the mixture exit at the bottom in stream 616 and follows to the hydrolysis column 618. Stream 614 is recycled back to column 604 and mixed with a fresh carbonyl make-up stream, giving rise to stream 606.

In addition to stream 616, water also is fed in column 618 as stream 620, and reacts with acetal to recover glycol. The original carbonyl species, also produced in this step, exit column 618 as stream 622, together with unconverted acetal and lights. The bottoms, leaving as 624, contain mainly water and glycol. Stream 622 may be recycled back to column 604, but it was not considered in this example.

Glycol from stream 624 is concentrated in column 626, where water leaves as a light contaminant in stream 1526. The bottoms 1528 correspond to enriched glycol, which may be further purified in additional distillation steps. While glycol is shown as a representative polyol in this example, it is envisioned that the process may be adapted to capture polyol species containing two or more available alcohol groups and two or more carbon atoms, such as monoethylene glycol and propylene glycol.

In this example, numeric values were attributed to the process to better illustrate how the separation sequence takes place, and the corresponding mass balances were organized in Tables 1 to 3. As the focus is on the recovery of ketones and glycols, only modules 200, 300, and 600 were represented, in such a way that stream 415 corresponds to the clarified fermented broth exiting module (400 in FIG. 4), and stream 1504 related to the off-gas produced in the fermenter.

TABLE 1

Mass balance in modules 200 and 300 in Example 5

| Streams | 1504 | 1506 | 1508 | 1510 | 1514 | 1512 | 1515 |
|---|---|---|---|---|---|---|---|
| | | | Component mass flow (kg/hr) | | | | |
| Acetone | 208.00 | 0 | 5.47 | 202.52 | 284.66 | 25.15 | 0.16 |
| IPA | 104.80 | 0 | 0 | 104.80 | 0.004 | 0 | 304.91 |
| Water | 171.20 | 15000 | 198.51 | 14972.69 | 1.34 | 0.10 | 19016.68 |
| Glycol | 0.07 | 0 | 0 | 0.07 | 0 | 0 | 0.07 |
| Acetic acid | 6.4 | 0 | 0 | 6.4 | 0 | 0 | 50.69 |
| Formic acid | 2.4 | 0 | 0 | 2.4 | 0 | 0 | 31.09 |
| Phenol | 0.037 | 0 | 0 | 0.037 | 0 | 0 | 74.08 |
| Glycerol | 0 | 0 | 0 | 0 | 0 | 0 | 0.00 |
| CO2 | 1526.38 | 0 | 1523.78 | 2.60 | 0.228 | 2.371 | 0.00 |
| N2 | 4899.14 | 0 | 4898.96 | 0.18 | 0.001 | 0.178 | 0.00 |
| O2 | 1081.59 | 0 | 1081.51 | 0.08 | 0.001 | 0.08 | 0.00 |
| Carbonyl | 0.00 | 0 | 0 | 0 | 0 | 0 | 0.00 |
| Acetal | 0.00 | 0 | 0 | 0 | 0 | 0 | 0.00 |
| Sugars + salts | 0 | 0 | 0 | 0 | 0 | 0 | 0.00 |

TABLE 2

Mass balance in module 600 in Example 5

| Streams | 415 | 1516 | 1520 | 1524 | 1525 | 606 | make-up | 608 | 610 |
|---|---|---|---|---|---|---|---|---|---|
| | | | | Component mass flow (kg/hr) | | | | | |
| Acetone | 109.27 | 107.44 | 1.83 | 1.82 | 0.01 | 0 | 0 | 0.01 | 0.00 |
| IPA | 205.90 | 200.12 | 5.79 | 5.70 | 0.09 | 0 | 0 | 0.09 | 0.00 |
| Water | 6270.92 | 4045.43 | 2225.50 | 1092.97 | 1132.53 | 0 | 0 | 296.80 | 1026.52 |
| Glycol | 821.79 | 0.00 | 821.79 | 0.14 | 821.66 | 0 | 0 | 0 | 164.33 |
| Acetic acid | 124.62 | 44.29 | 80.34 | 22.22 | 58.12 | 0 | 0 | 0.03 | 58.09 |
| Formic acid | 46.06 | 28.69 | 17.37 | 8.02 | 9.35 | 0 | 0 | 1.94 | 7.41 |
| Phenol | 195.06 | 74.04 | 121.02 | 19.13 | 101.89 | 0 | 0 | 1.92 | 99.97 |
| Glycerol | 15.35 | 0.00 | 15.35 | 0.00 | 15.35 | 0 | 0 | 0 | 15.35 |
| CO2 | 0 | 0 | 0 | 0 | 0 | 0 | 0 | 0 | 0 |
| N2 | 0 | 0 | 0 | 0 | 0 | 0 | 0 | 0 | 0 |
| O2 | 0 | 0 | 0 | 0 | 0 | 0 | 0 | 0 | 0 |
| Carbonyl | 0 | 0 | 0 | 0 | 0 | 5832.68 | 467 | 5366.15 | 0.00 |
| Acetal | 0 | 0 | 0 | 0 | 0 | 0 | 0 | 933.07 | 0.00 |
| Sugars + salts | 1211.02 | 0.00 | 1211.02 | 0.00 | 1211.02 | 0 | 0 | 0 | 1211.02 |

TABLE 3

| Mass balance in module 600 in Example 5 (continued) | | | | | | | |
|---|---|---|---|---|---|---|---|
| Streams | 614 | 616 | 620 | 622 | 624 | 1526 | 1528 |
| | | Component mass flow (kg/hr) | | | | | |
| Acetone | 0.00 | 0.01 | 0 | 0.01 | 0.00 | 0 | 0 |
| IPA | 0 | 0.09 | 0 | 0.09 | 0.00 | 0 | 0 |
| Water | 0.19 | 296.61 | 763.34 | 16.34 | 871.91 | 871.91 | 0 |
| Glycol | 0 | 0 | 0 | 0 | 591.59 | 0.12 | 591.47 |
| Acetic acid | 0.00 | 0.03 | 0 | 0.00 | 0.029 | 0.029 | 0 |
| Formic acid | 0 | 1.94 | 0 | 0.04 | 1.90 | 1.90 | 0 |
| Phenol | 0 | 1.92 | 0 | 0.004 | 1.92 | 1.89 | 0.031 |
| Glycerol | 0 | 0 | 0 | 0 | 0 | 0 | 0 |
| CO2 | 0 | 0 | 0 | 0 | 0 | 0 | 0 |
| N2 | 0 | 0 | 0 | 0 | 0 | 0 | 0 |
| O2 | 0 | 0 | 0 | 0 | 0 | 0 | 0 |
| Carbonyl | 5365.81 | 0.33 | 0 | 420.22 | 0 | 0 | 0 |
| Acetal | 0 | 933.07 | 0 | 93.30 | 0 | 0 | 0 |
| Sugars + salts | 0 | 0 | 0 | 0 | 0 | 0 | 0 |

Example 6: Reactive Extraction

In the next example, separation of glycols and ketones from the microbial fermentation broth is performed by reactive extraction. While conceptually similar to reactive distillation, reactive extraction differs by the method by which acetal is isolated from the mixture. In both cases, a carbonyl species is introduced converting glycol into an acetal. However, reactive extraction utilizes solvent addition to extract the acetal at the organic phase.

Solvents employed in this operation should be selected considering their affinity with the acetal produced, facilitating partition from the aqueous phase; solvent may include mutual solvents having partial miscibility with water. Possible options include toluene, ethylbenzene and o-xylene. In some embodiments, the organic phase—solvent, acetal, carbonyl and other contaminants—leaves the column as a top stream, while the aqueous—water, solubilized salts and sugars, part of the organics—remain at the bottom.

Figure 16:
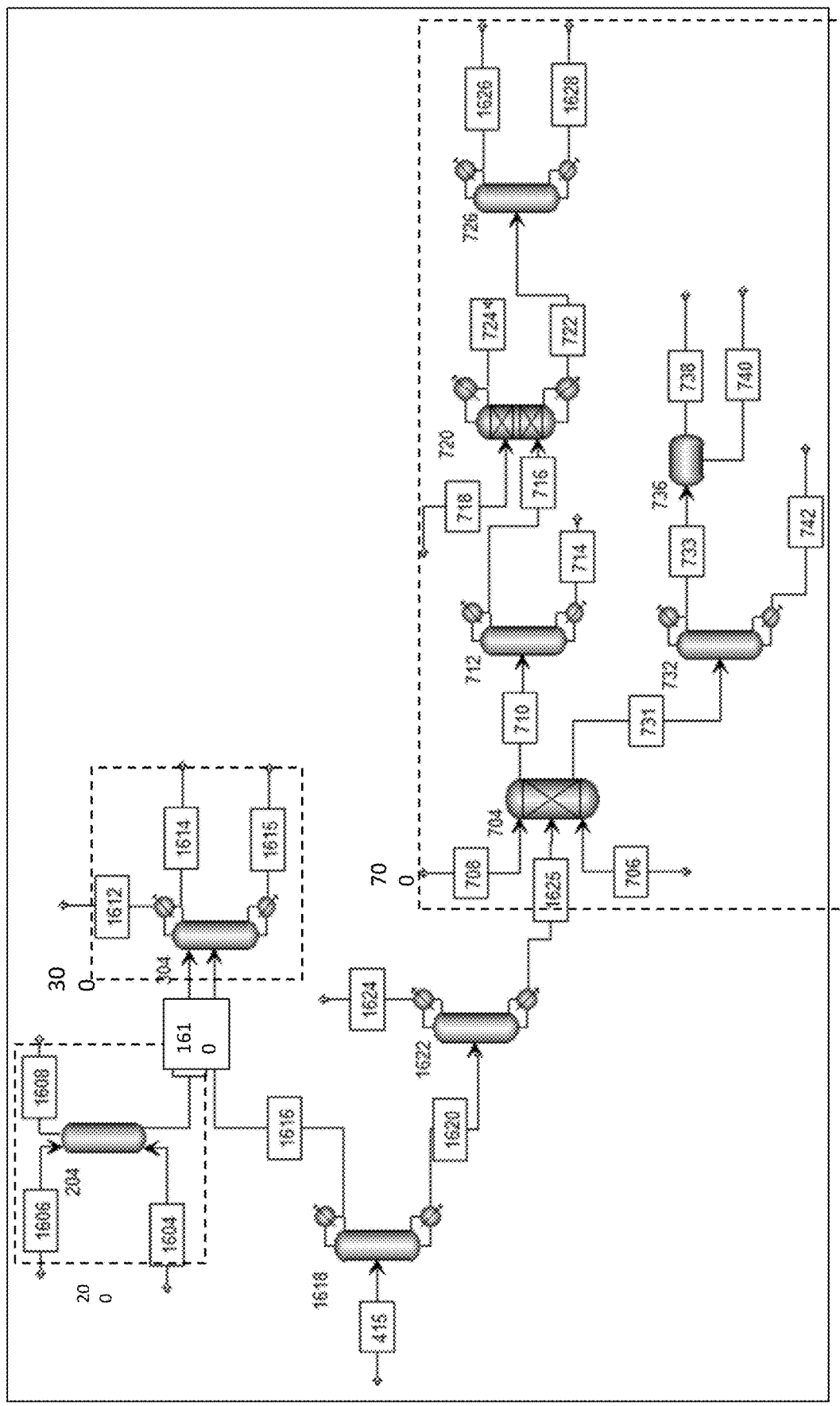
FIG. 16 is a flow diagram of a reactive extraction process in accordance with embodiments of the present disclosure.

With particular respect to FIG. 16, an off-gas stream 1604, generated during fermentation, is transferred to absorption module 200 (dashed box) described in greater detail in FIG. 2 and the accompanying text. Column 204 within module 200 utilizes input water 1606 to absorb ketones and other compounds, which exit as stream 1610. Incondensable gases 1608 are also obtained as products from the absorption column 204.

Stream 1610 is then directed to module 300 (dashed box), where the ketone is recovered as described in FIG. 3 and the accompanying text (represented as column 304 in this example). Most of the ketone product is obtained in stream 1614, while remaining incondensable gases leave in 1612 (in some embodiments, this stream may be recycled back to module 200). The bottoms 1615 of the ketone recovery column 304, which may contain the solvent (such as water), acids, and glycols, may be sent to wastewater treatment or may be treated to remove the contaminants from the solvent, which may be recirculated back to the absorption column 204 in some embodiments.

Broth stream 415 may be obtained from a fermenter and sent to column 1618, where volatiles present in the liquid mixture are stripped and obtained as 1616. This stream may be sent to column 304 in order to further concentrate the ketone products. In some embodiments, stream 415 may be pretreated using a pretreatment module (not shown, but 400 in FIG. 4) to remove cells and a portion of solids and salts prior to transfer.

The bottoms 1620, including glycols and other products of interest, are transferred to distillation column 1622, where part of the water present is removed as 1624. This concentration step can be accomplished either by single or multiple effect distillation columns, or by a series of evaporators, depending on the feasibility of removing water without significant loss of products; in this example, one column was sufficient. A stream enriched in glycols is obtained as a bottoms product, 1625.

While not illustrated, in some configurations, glycol enriched stream 1625 may be sent to a hydrogenation reactor after the concentration step, where a catalyst uses a small flow of oxygen to hydrogenate color contaminants and UV absorbers.

Subsequently, glycol enriched stream 1625 may be sent to a distillation column such as 704, represented in module 700, described in greater detail in FIG. 7 and the accompanying text. While also not illustrated, it is envisioned that stream 1625 is sent to an activated carbon bed prior to distillation column 704, which is also capable of reducing color and odor. Removal of color and UV absorbing contaminants from glycol enriched stream 1625 may also be performed in an activated carbon bed following module 700.

In this specific example, however, the optional hydrogenation step was not performed, and bottoms 1625 are transferred directly to reactive extraction column 704 in module 700, as described in FIG. 7 and accompanying text. Stream 706 including carbonyl species was introduced in the column, where it reacted with glycol to form acetal. Solvent 708 was added to the equipment to simultaneously extract acetal from the liquid mixture, essentially in the organic phase.

Acetal, unreacted carbonyl, solvent, and other organics exit the column as 710, while water, unreacted glycol, solubilized salts and sugars are obtained as bottoms 731. The aqueous phase 731 was transferred to distillation column 732, equipped with condenser and a decanter 736, which partially recovers solvent. For example, bottoms 731 may be separated into an overhead stream 733, which may be cooled using heat exchanger 734 and passed to decanter 736 to separate the overhead stream 733 into a fraction 738 containing organics such as aldehydes, ketones, acetals, and solvent, and a water fraction 740. Water and other heavies that exit column 732 as the bottoms may be recovered as stream 742.

The organic stream 710 from column 704 follows to distillation column 712, where heavy components, like solvent and unreacted glycol, exit as stream 714. Light components such as the carbonyl species and acetal are removed as 716, which is sent to the reactive distillation column 720. In some embodiments, stream 714 is recycled back to the column 704.

In column 720, water is introduced as 718, and reacts with acetal to recover glycol and the original carbonyl species. The carbonyl, as well as unreacted acetal, leave as top steam 724, while a glycol enriched stream 722 is obtained in the bottom. In some embodiments, stream 724 is recycled back to column 704.

Finally, stream 722 is sent to column 726 for further concentration of glycol. Water and other light components are removed in 1626, while glycol exits as 1628. This stream may be processed in subsequent distillation columns for obtainment of a purer product. While glycol is shown as a representative polyol in this example, it is envisioned that the process may be adapted to capture polyol species containing two or more available alcohol groups and two or more carbon atoms, such as monoethylene glycol and propylene glycol.

In the example, numeric values were attributed and simulated using Aspen Plus® to better illustrate how the separation sequence takes place, and the corresponding mass balances are organized in Tables 4 to 8. As the focus is on the recovery of ketones and glycols, only modules 200, 300, and 700 were represented, in such a way that stream 415 corresponds to the clarified fermented broth exiting module (400 in FIG. 4), and stream 1604 related to the off-gas produced in the fermenter.

TABLE 4

Mass balance for modules 200 and 300 in Example 6

| Streams | 1604 | 1606 | 1608 | 1610 | 1612 | 1614 | 1615 |
|---|---|---|---|---|---|---|---|
| | | | Components mass flow (kg/hr) | | | | |
| Acetone | 208.00 | 0 | 5.473 | 202.52 | 0.29 | 309.67 | 0 |
| IPA | 104.80 | 0 | 0 | 104.80 | 0.11 | 304.81 | 0 |
| Water | 171.20 | 15000 | 198.51 | 14972.69 | 0.078 | 2462.01 | 16556.028 |
| Glycol | 0.066 | 0 | 0 | 0.066 | 0 | 0 | 0.066 |
| Acetic acid | 6.40 | 0 | 0 | 6.40 | 0 | 0 | 50.69 |
| Formic acid | 2.40 | 0 | 0 | 2.40 | 0 | 2.905 | 28.18 |
| Phenol | 0.037 | 0 | 0 | 0.037 | 0 | 58.27 | 15.81 |
| Glycerol | 0 | 0 | 0 | 0 | 0 | 0 | 0 |
| CO2 | 1526.38 | 0 | 1523.78 | 2.60 | 0.64 | 1.96 | 0 |
| N2 | 4899.14 | 0 | 4898.96 | 0.18 | 0.16 | 0.016 | 0 |
| O2 | 1081.59 | 0 | 1081.51 | 0.076 | 0.065 | 0.011 | 0 |
| Carbonyl | 0 | 0 | 0 | 0 | 0 | 0 | 0 |
| Toluene | 0 | 0 | 0 | 0 | 0 | 0 | 0 |
| Acetal | 0 | 0 | 0 | 0 | 0 | 0 | 0 |
| Sugars + salts | 0 | 0 | 0 | 0 | 0 | 0 | 0 |

TABLE 5

Mass balance for columns 1618 and 1622 in Example 6

| Streams | 415 | 1616 | 1620 | 1624 | 1625 |
|---|---|---|---|---|---|
| | | Components mass flow (kg/hr) | | | |
| Acetone | 109.27 | 107.44 | 1.83 | 1.82 | 0.01 |
| IPA | 205.90 | 200.12 | 5.79 | 5.70 | 0.09 |
| Water | 6270.92 | 4045.43 | 2225.50 | 1092.97 | 1132.53 |
| Glycol | 821.79 | 0 | 821.79 | 0.14 | 821.66 |
| Acetic acid | 124.62 | 44.29 | 80.34 | 22.22 | 58.12 |
| Formic acid | 46.06 | 28.69 | 17.37 | 8.02 | 9.35 |
| Phenol | 195.06 | 74.04 | 121.02 | 19.13 | 101.89 |
| Glycerol | 15.35 | 0 | 15.35 | 0 | 15.35 |
| CO2 | 0 | 0 | 0 | 0 | 0 |
| N2 | 0 | 0 | 0 | 0 | 0 |
| O2 | 0 | 0 | 0 | 0 | 0 |
| Carbonyl | 0 | 0 | 0 | 0 | 0 |
| Toluene | 0 | 0 | 0 | 0 | 0 |
| Acetal | 0 | 0 | 0 | 0 | 0 |
| Sugars + salts | 1211.02 | 0 | 1211.02 | 0 | 1211.02 |

TABLE 6

Mass balance for columns 704 and 712 for Example 6

| Streams | 706 | 708 | 710 | 731 | 714 | 716 |
|---|---|---|---|---|---|---|
| | | Components mass flow (kg/hr) | | | | |
| Acetone | 0 | 0 | 0.01 | 0.00 | 0 | 0.01 |
| IPA | 0 | 0 | 0.076 | 0.009 | 0 | 0.076 |
| Water | 0 | 0 | 363.92 | 959.39 | 214.29 | 149.63 |
| Glycol | 0 | 0 | 88.80 | 75.54 | 88.80 | 0 |
| Acetic acid | 0 | 0 | 38.90 | 19.22 | 38.90 | 0 |

TABLE 6-continued

Mass balance for columns 704 and 712 for Example 6

| Streams | 706 | 708 | 710 | 731 | 714 | 716 |
|---|---|---|---|---|---|---|
| | | | Components mass flow (kg/hr) | | | |
| Formic acid | 0 | 0 | 5.10 | 4.25 | 5.03 | 0.072 |
| Phenol | 0 | 0 | 100.19 | 1.70 | 100.19 | 0 |
| Glycerol | 0 | 0 | 9.24 | 6.12 | 9.24 | 0 |
| CO2 | 0 | 0 | 0 | 0 | 0 | 0 |
| N2 | 0 | 0 | 0 | 0 | 0 | 0 |
| O2 | 0 | 0 | 0 | 0 | 0 | 0 |
| Carbonyl | 5832.64 | 0 | 5366.10 | 0 | 0 | 5366.10 |
| Toluene | 0 | 1000 | 999.03 | 0.97 | 996.75 | 2.28 |
| Acetal | 0 | 0 | 933.07 | 0 | 1.24 | 931.83 |
| Sugars + salts | 0 | 0 | 0 | 1211.017 | 0 | 0 |

TABLE 7

Mass balance for columns 720 and 726 in Example 6

| Streams | 718 | 724 | 722 | 1626 | 1628 |
|---|---|---|---|---|---|
| | | Components mass flow (kg/hr) | | | |
| Acetone | 0 | 0.01 | 0 | 0 | 0 |
| IPA | 0 | 0.076 | 0 | 0 | 0 |
| Water | 760.85 | 119.01 | 619.99 | 0 | 619.99 |
| Glycol | 0 | 0 | 590.80 | 585.85 | 4.95 |
| Acetic acid | 0 | 0 | 0 | 0 | 0 |
| Formic acid | 0 | 0.018 | 0.054 | 0 | 0.054 |
| Phenol | 0 | 0 | 0 | 0 | 0 |
| Glycerol | 0 | 0 | 0 | 0 | 0 |
| CO2 | 0 | 0 | 0 | 0 | 0 |
| N2 | 0 | 0 | 0 | 0 | 0 |
| O2 | 0 | 0 | 0 | 0 | 0 |
| Carbonyl | 0 | 5785.43 | 0 | 0 | 0 |
| Toluene | 0 | 2.28 | 0 | 0 | 0 |
| Acetal | 0 | 93.18 | 0 | 0 | 0 |
| Sugars + salts | 0 | 0 | 0 | 0 | 0 |

TABLE 8

Mass balance for columns 732 and 736 in Example 6

| Streams | 742 | 733 | 738 | 740 |
|---|---|---|---|---|
| | Components mass flow (kg/hr) | | | |
| Acetone | 0 | 0.001 | 0 | 0.001 |
| IPA | 0 | 0.009 | 0 | 0.009 |
| Water | 910.97 | 48.43 | 0.002 | 48.42 |
| Glycol | 75.54 | 0 | 0 | 0 |
| Acetic acid | 18.91 | 0.30 | 0 | 0.30 |
| Formic acid | 4.04 | 0.21 | 0 | 0.21 |
| Phenol | 1.61 | 0.09 | 0.001 | 0.09 |
| Glycerol | 6.12 | 0 | 0 | 0 |
| CO2 | 0 | 0 | 0 | 0 |
| N2 | 0 | 0 | 0 | 0 |
| O2 | 0 | 0 | 0 | 0 |
| Carbonyl | 0 | 0 | 0 | 0 |
| Toluene | 0 | 0.97 | 0.77 | 0.19 |
| Acetal | 0 | 0 | 0 | 0 |
| Sugars + salts | 1211.02 | 0 | 0 | 0 |

Example 7: Thin-Film Evaporation

Figure 17:
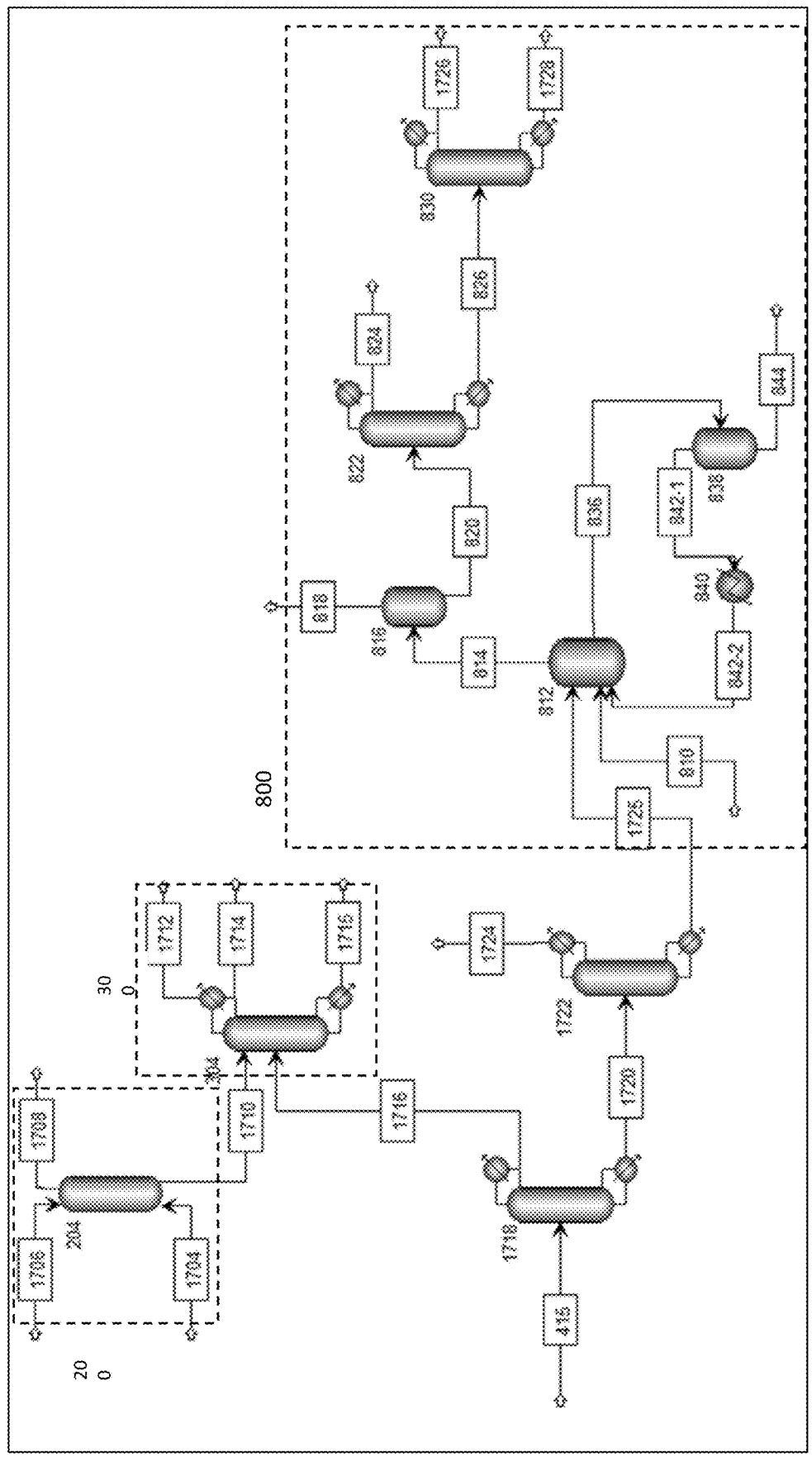
FIG. 17 is a flow diagram of a thin-film evaporation process in accordance with embodiments of the present disclosure.

In the next example, a process in accordance with the present disclosure is used to isolate ketones and glycols from the microbial fermentation broth using thin-film evaporation. With particular respect to FIG. 17, a fermented broth is transferred as stream 415 to distillation column 1718. In some embodiments, stream 415 may be processed by a pretreatment module (not shown) such as that described in FIG. 4 and accompanying text to remove cells and insoluble solids. However, in some embodiments, broth from fermentation may be fed directly into column 1718. Distillation column 1718 separates light components—including ketones—as top product 1716, while heavies, such as glycol, exit as 1720.

Stream 1716 is then sent to module 300 (represented as a dashed box and described above with respect to FIG. 3 and the accompanying text), where column 304 separates ketones as 1714, while heavy organics and water leave as 1715 and a small quantity of non-condensable gases leave as 1712. In some embodiments, this stream may be recycled back to module 200. The bottoms 1715 of the ketone recovery column 304 may be sent to wastewater treatment or may be treated to remove the contaminants from the solvent, which may be recirculated back to the absorption column 204 in some embodiments.

In addition, off-gas stream 1704, generated during fermentation, is transferred to absorption module 200, which is described in FIG. 2 and the accompanying text. Column 204 within module 200 utilizes input water 1706 to absorb ketones and other compounds, which exit as stream 1710. Incondensable gases 1708 are also obtained as products from the absorption column 204. In column 304, stream 1710 is also processed, including liquid products recovered in adsorption column 204, which separates them from incondensable gases contained in the fermentation off-gas.

Glycol present in stream 1720 is directed to column 1722 as a pre-concentration step. This can be accomplished either by single or multiple effect distillation columns, or by a series of evaporators, depending on the feasibility of removing water without significant loss of products; in this example, one column was sufficient. A stream enriched in glycols is obtained as a bottoms product, 1725, while water leaves as 1724.

While not illustrated, in some configurations, glycol enriched stream 1725 may optionally be sent to a hydrogenation reactor after the concentration step, where a catalyst uses a small flow of oxygen to hydrogenate color contaminants and UV absorbers. Subsequently, glycol enriched stream 1725 may be sent to a thin-film evaporator such as 812, represented in module 800, described with respect to FIG. 8 and the accompanying text. While not illustrated, it is envisioned that stream 1725 may be sent to an activated carbon bed, which is also capable of reducing color and odor, prior to thin-film evaporator 812. Removal of color and UV absorbers contaminants can also be performed in an activated carbon bed following module 800, that is, processing glycol enriched stream 1725.

In this specific example, however, the hydrogenation step was not performed, and bottoms 1725 followed directly to thin-film evaporator 812 in module 800, as described in FIG. 8 and accompanying text. A salt entrainer is also added to 812 as make-up stream 810. Stream 814 obtained as overhead, rich in glycol, is sent to partial condenser 816, where light organics and water exit as 818. Stream 820 is the heavier product from partial condenser 816. It comprises glycol and is fed into to distillation column 822, where light contaminants are further removed as stream 824.

The bottoms 826 from distillation column 822 are sent to column 830 for removal of heavier organics, which exit as 1728, and purified glycol is obtained as 1726. While glycol is shown as a representative polyol in this example, it is envisioned that the process may be adapted to capture polyol species containing two or more available alcohol groups and two or more carbon atoms, such as monoethylene glycol and propylene glycol.

Stream 836, also produced in thin-film evaporator 812, constitutes a mixture of entrainer, residual glycol, sugars and salts. In order to recover the entrainer, this stream is sent to the second thin-film evaporator 838, which operates at low pressure. Sugars and salts exit in the liquid phase as 844, considered a waste stream in some embodiments. Residual glycol and entrainer are removed as 842-1, later cooled down in heat exchanger 840, and recycled back to thin-film evaporator 812 as 842-2.

In this example, numeric values were attributed and simulated using Aspen Plus® to better illustrate how the separation sequence takes place, and the corresponding mass balances are organized in Tables 9 to 12. As the focus is on the recovery of ketones and glycols, only modules 200, 300, and 800 were represented, in such a way that stream 415 corresponds to the clarified fermented broth exiting module (400 in FIG. 4), and stream 1704 related to the off-gas produced in the fermenter.

TABLE 9

Mass balance for modules 200 and 300 in Example 7

| Streams | 1704 | 1706 | 1708 | 1710 | 1712 | 1714 | 1715 |
|---|---|---|---|---|---|---|---|
| | | | Component mass flow (kg/h) | | | | |
| Acetone | 208.00 | 0 | 5.43 | 202.56 | 25.77 | 283.96 | 0.27 |
| IPA | 104.80 | 0 | 0.28 | 104.52 | 0 | 0.005 | 303.66 |
| H2O | 171.20 | 15000 | 198.82 | 14972.38 | 0.10 | 1.34 | 19017.29 |
| Glycol | 0.07 | 0 | 0 | 0.066 | 0 | 0 | 0.066 |
| Acetic acid | 6.40 | 0 | 0 | 6.40 | 0 | 0 | 50.78 |
| Formic acid | 2.40 | 0 | 0 | 2.40 | 0 | 0 | 31.09 |
| Phenol | 0.04 | 0 | 0 | 0.037 | 0 | 0 | 74.02 |
| Entrainer | 0 | 0 | 0 | 0 | 0 | 0 | 0 |
| CO2 | 1526.38 | 0 | 1523.72 | 2.66 | 2.43 | 0.23 | 0 |
| N2 | 4899.14 | 0 | 4898.96 | 0.18 | 0.18 | 0.001 | 0 |
| O2 | 1081.59 | 0 | 1081.51 | 0.077 | 0.077 | 0.001 | 0 |
| Sugars + salts | 0 | 0 | 0 | 0 | 0 | 0 | 0 |

TABLE 10

Mass balance for columns 1718 and 1724 in Example 7

| Streams | 415 | 1716 | 1720 | 1724 | 1725 |
|---|---|---|---|---|---|
| | | Component mass flow (kg/h) | | | |
| Acetone | 109.27 | 107.44 | 1.83 | 1.82 | 0.01 |
| IPA | 205.90 | 199.15 | 6.75 | 6.54 | 0.21 |
| H2O | 6270.92 | 4046.35 | 2224.57 | 1099.91 | 1124.66 |
| Glycol | 821.79 | 0 | 821.79 | 0.18 | 821.62 |
| Acetic acid | 124.62 | 44.38 | 80.24 | 19.82 | 60.43 |
| Formic acid | 46.06 | 28.69 | 17.37 | 2.36 | 15.01 |
| Phenol | 195.06 | 73.99 | 121.08 | 19.38 | 101.70 |
| Entrainer | 15.35 | 0 | 15.35 | 0 | 15.35 |
| CO2 | 0 | 0 | 0 | 0 | 0 |
| N2 | 0 | 0 | 0 | 0 | 0 |
| O2 | 0 | 0 | 0 | 0 | 0 |
| Sugars + salts | 1211.02 | 0 | 1211.02 | 0 | 1211.02 |

TABLE 11

Mass balance for 812 and 838 in Example 7

| Streams | 810 | 814 | 836 | 842-1 | 844 | 842-2 |
|---|---|---|---|---|---|---|
| | | Component mass flow (kg/h) | | | | |
| Acetone | 0 | 0.01 | 0 | 0 | 0 | 0 |
| IPA | 0 | 0.21 | 0 | 0 | 0 | 0 |
| H2O | 0 | 1124.59 | 6.06 | 5.99 | 0.07 | 5.99 |
| Glycol | 0 | 801.15 | 157.17 | 136.70 | 20.47 | 136.70 |
| Acetic acid | 0 | 60.42 | 0.51 | 0.50 | 0.01 | 0.50 |
| Formic acid | 0 | 15.01 | 0.08 | 0.07 | 0.001 | 0.07 |
| Phenol | 0 | 101.00 | 8.31 | 7.61 | 0.71 | 7.61 |
| Entrainer | 100 | 10.13 | 138.83 | 33.60 | 105.22 | 33.60 |

TABLE 11-continued

Mass balance for 812 and 838 in Example 7

| Streams | 810 | 814 | 836 | 842-1 | 844 | 842-2 |
|---|---|---|---|---|---|---|
| | | | Component mass flow (kg/h) | | | |
| CO2 | 0 | 0 | 0 | 0 | 0 | 0 |
| N2 | 0 | 0 | 0 | 0 | 0 | 0 |
| O2 | 0 | 0 | 0 | 0 | 0 | 0 |
| Sugars + salts | 0 | 0.015 | 1213.36 | 2.36 | 1211.00 | 2.36 |

TABLE 10

Mass balance for 816, 822, and 830 in Example 7

| Streams | 818 | 820 | 824 | 826 | 1726 | 1728 |
|---|---|---|---|---|---|---|
| | | | Component mass flow (kg/h) | | | |
| Acetone | 0.01 | 0 | 0 | 0 | 0 | 0 |
| IPA | 0.07 | 0.13 | 0.13 | 0 | 0 | 0 |
| H2O | 364.47 | 760.13 | 7604.13 | 0 | 0 | 0 |
| Glycol | 1.73 | 799.41 | 25.23 | 774.19 | 760.00 | 14.19 |
| Acetic acid | 8.51 | 51.91 | 51.91 | 0 | 0 | 0 |
| Formic acid | 1.43 | 13.58 | 13.58 | 0 | 0 | 0 |
| Phenol | 1.97 | 99.03 | 99.02 | 0.003 | 0.003 | 0 |
| Entrainer | 0 | 10.13 | 0 | 10.13 | 0 | 10.13 |
| CO2 | 0 | 0 | 0 | 0 | 0 | 0 |
| N2 | 0 | 0 | 0 | 0 | 0 | 0 |
| O2 | 0 | 0 | 0 | 0 | 0 | 0 |
| Sugars + salts | 0 | 0.015 | 0 | 0.015 | 0 | 0.015 |

Although the preceding description is described herein with reference to particular means, materials and embodiments, it is not intended to be limited to the particulars disclosed herein; rather, it extends to all functionally equivalent structures, methods and uses, such as are within the scope of the appended claims. In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. § 112(f) for any limitations of any of the claims herein, except for those in which the claim expressly uses the words 'means for' together with an associated function.

What is claimed is:

1. A method of obtaining ketones from a fermentation process, the method comprising:
    collecting an off-gas and a fermented broth from a fermenter, wherein the off-gas and the fermented broth both comprise a ketone;
    transferring the off-gas from the fermenter to a ketone recuperation module and the fermented broth to a fluid separating module; and
    isolating the ketones from both the off-gas and the fermented broth.

2. The method of claim 1, further comprising processing the fermented broth with one or more selected from a group consisting of activated carbon bed, hydrogenation, UV treatment, and ion-exchange column.

3. The method of claim 1, further comprising transferring the fermented broth to a color and odor module prior to or following the fluid separation module.

4. The method of claim 1, further comprising transferring the fermented broth to a concentration module prior to transferring the fermented broth to the fluid separation module.

5. The method of claim 4 wherein the concentration module comprises one or more selected from a group consisting of distillation columns and evaporators.

6. The method of claim 1, further comprising transferring the fermented broth to a pretreatment module prior to transferring the fermented broth to the fluid separation module, and wherein the pretreatment module removes at least a portion of cells and solids from the fermented broth.

7. The method of claim 6, wherein the pretreatment module comprises one or more selected from a group consisting of centrifugation, microfiltration, ultrafiltration, and nanofiltration.

8. The method of claim 1, wherein the fluid separating module comprises a salt removal module and one or more distillation columns.

9. The method of claim 8, wherein the salt removal module comprises one or more selected from a group consisting of an ion exchange module, a precipitation module, an electrodialysis module, and a nanofiltration module.

10. The method of claim 1, wherein the ketone is acetone.

11. The method of claim 1, further comprising transferring the off-gas from the fermenter to a gas separating module prior to transferring the off-gas to the ketone recuperation module, wherein the gas separating module removes at least a portion of the ketone from the off-gas.

12. A method of obtaining ketones from a fermentation process, the method comprising:
    collecting an off-gas and a fermented broth from the fermenter, wherein the off-gas and the fermented broth both comprise a ketone;
    transferring the off-gas from the fermenter to a ketone recuperation module;
    transferring the fermented broth to a light organic separation module that generates a stream comprising the ketone;
    transferring the stream comprising the ketone to the ketone recuperation module; and
    isolating the ketone from both the off-gas and the fermented broth.

13. The method of claim 12, further comprising processing the fermented broth with one or more selected from a group consisting of activated carbon bed, hydrogenation, UV treatment, and ion-exchange column.

14. The method of claim 12, further comprising transferring the fermented broth to a color and odor module prior to or following the light organic separation module.

15. The method of claim 12, further comprising transferring the fermented broth to a concentration module prior to transferring the fermented broth to the light organic separation module.

16. The method of claim 15 wherein the concentration module comprises one or more selected from a group consisting of distillation columns and evaporators.

17. The method of claim 12, further comprising transferring the fermented broth to a pretreatment module prior to transferring the fermented broth to the light organic separation module, and wherein the pretreatment module removes at least a portion of cells and solids from the fermented broth.

18. The method of claim 17, wherein the pretreatment module comprises one or more selected from a group consisting of centrifugation, microfiltration, ultrafiltration, and nanofiltration.

19. The method of claim 12, wherein the ketone is acetone.

20. The method of claim 12, further comprising transferring the off-gas from the fermenter to a gas separating module prior to transferring the off-gas to the ketone recuperation module, wherein the gas separating module removes at least a portion of the ketone from the off-gas.

21. A method of obtaining glycols from a fermentation process, the method comprising:
collecting a fermented broth from the fermenter, wherein the fermented broth comprises a glycol;
transferring the fermented broth to a fluid separating module that comprises a reactive distillation column; and
isolating the glycol from the fermented broth,
wherein isolating the glycol comprises:
reacting a glycol in the fermented broth in the reactive distillation column with a separating agent to form an acetal and collecting a stream from the reactive distillation column comprising the acetal;
transferring the stream comprising the acetal to a distillation column and distilling the stream comprising the acetal;
transferring the stream comprising the acetal from the distillation column to a hydrolysis column and hydrolyzing the acetal to yield a reverted glycol; and
collecting a stream from the hydrolysis column comprising the reverted glycol.

22. The method of claim 21, wherein the glycol is monoethylene glycol.

23. The method of claim 21, wherein the fluid separating module comprises a first evaporator, and wherein the fermented broth comprises a salt entrainer; wherein the method further comprises:
collecting a stream from the first evaporator comprising a glycol.

24. The method of claim 23, wherein the salt entrainer is glycerol or sugar.

25. The method of claim 23, further comprising:
transferring the stream from the first evaporator to a second evaporator;
collecting a stream from the second evaporator comprising a glycol.

26. The method of claim 23, comprising processing the stream from the first evaporator to remove one or more selected from a group consisting of water salt entrainer, heavy organics, and light organics.

27. The method of claim 23, wherein the evaporator is a thin film evaporator or a short path evaporator.

28. The method of claim 21, comprising processing the fermented broth with one or more selected from a group consisting of activated carbon bed, hydrogenation, UV treatment, and ion-exchange column.

29. The method of claim 21, comprising transferring the fermented broth to a color and odor module prior to or following the fluid separating module.

30. The method of claim 21, further comprising transferring the fermented broth to a concentration module prior to transferring the fermented broth to the fluid separating module.

31. The method of claim 30, wherein the concentration module comprises one or more selected from a group consisting of distillation columns and evaporators.

32. The method of claim 21, further comprising transferring the fermented broth to a pretreatment module prior to transferring the fermented broth to the fluid separating module, and wherein the pretreatment module removes at least a portion of cells and solids from the fermented broth.

33. The method of claim 32, wherein the pretreatment module comprises one or more selected from a group consisting of centrifugation, microfiltration, ultrafiltration, and nanofiltration.

34. The method of claim 21, wherein the fluid separating module comprises a salt removal module.

35. The method of claim 34, wherein the salt removal module comprises one or more selected from a group consisting of an ion exchange module, a precipitation module, an electrodialysis module, and a nanofiltration module.

36. The method of claim 21, further comprising collecting a stream comprising the separating agent from the hydrolysis column; and recycling at least a portion of the stream comprising the separating agent back to the reactive distillation column.

* * * * *